United States Patent
Sakairi et al.

(10) Patent No.: US 6,723,286 B2
(45) Date of Patent: Apr. 20, 2004

(54) CHEMICAL MONITORING METHOD AND APPARATUS, AND INCINERATOR

(75) Inventors: Minoru Sakairi, Tokorozawa (JP); Yoshiaki Kato, Mito (JP); Mamoru Mizumoto, Hitachinaka (JP); Yuichiro Hashimoto, Kokubunji (JP); Jiro Tokita, Sagamihara (JP); Masao Suga, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 171 days.

(21) Appl. No.: 09/987,094

(22) Filed: Nov. 13, 2001

(65) Prior Publication Data

US 2002/0048818 A1 Apr. 25, 2002

Related U.S. Application Data

(63) Continuation of application No. 09/447,577, filed on Nov. 23, 1999, now abandoned.

(30) Foreign Application Priority Data

Nov. 25, 1998 (JP) ............................................ 10-333680

(51) Int. Cl.[7] ........................ G01N 30/00; G01N 33/00; H01J 49/10
(52) U.S. Cl. ........................ 422/62; 250/281; 250/282; 250/287; 250/288; 422/88; 436/124; 436/173
(58) Field of Search ........................ 436/173, 124–126; 422/62, 88; 250/281, 282, 287–288

(56) References Cited

U.S. PATENT DOCUMENTS

| | | |
|---|---|---|
| 4,986,197 A | 1/1991 | Kent |
| 5,206,176 A | 4/1993 | Beer et al. |
| 5,415,025 A | 5/1995 | Bartman et al. |
| 5,571,478 A | 11/1996 | Bartman et al. |
| 5,597,535 A * | 1/1997 | Schaedlich et al. ............ 422/88 |
| 5,756,996 A | 5/1998 | Bier et al. |
| 5,879,948 A * | 3/1999 | Van Pelt et al. ............... 436/81 |
| 6,483,108 B1 * | 11/2002 | Sakairi ........................ 250/288 |

FOREIGN PATENT DOCUMENTS

| | | |
|---|---|---|
| DE | 4444524 | 6/1996 |
| JP | 4-161849 | 6/1992 |
| JP | 5-312796 | 11/1993 |
| JP | 7-155731 | 6/1995 |
| JP | 9-015229 | 1/1997 |
| JP | 9-243601 | 9/1997 |
| JP | 11-304760 | 11/1999 |
| WO | 98/11595 | * 3/1998 |

OTHER PUBLICATIONS

Takeshita, R. et al, Environmental Science and Technology 1995, 29, 1186–1194.*
Catinella, S. et al, Rapid Communications in Mass Spectrometry 1995, 9, 1302–1309.*

(List continued on next page.)

Primary Examiner—Arlen Soderquist
(74) Attorney, Agent, or Firm—Mattingly, Stanger & Malur, P.C.

(57) ABSTRACT

There was previously no monitoring method and monitoring apparatus which could measure dioxins at ppt levels and dioxin precursors at ppb levels with high sensitivity.

According to this invention, organic and inorganic compounds containing highly electronegative elements are selectively ionized by atmospheric pressure chemical ionization, the ions produced are detected by a mass spectrometer, and their amount is measured.

As a result, interfering substances such as nitrogen, air, hydrocarbons and carbon dioxide which are the main components of flue gas are eliminated, and dioxins or organochlorine compounds such as dioxin precursors can be selectively monitored.

3 Claims, 28 Drawing Sheets-

OTHER PUBLICATIONS

Grochowalski, A, et al, Chemical Abstracts 1996, 124, abstract 14179f.*

Brinkman, M. C. et al, Chemical Abstracts 1999, 131, abstract 160755b.*

L. Cassitto et al, Inquinamento 1977, 19, 33–38.

S. Asada et al, Chemosphere 1987, 16, 1907–1910.

S.A. McLuckey et al, Anal. Chem. 1988, 60, 2220–2227.

S.N. Ketkar et al, Anal. Chem. 1989, 61, 260–264.

"Bunseki", 1998, pp. 512–519.

Pharmacia vol. 34, No. 5, 1998, pp. 441–444.

Waste Incineration Technology, Ohm Co., 1995, pp. 88–92.

Y. Hanai et al., "Automatic Analysis of Chlorobenzenes in the Exhaust Gas from MSW Incineration Plant", Yokohama National University Environmental Research Abstracts, vol. 18, 1992, pp. 1–8.

D.E. Durbin et al, J. Am. Chem. Soc. 1970, 92, pp. 5131–5136.

L. Cassitto et al, Chem. Abstr. 1978, 88. abstract 1134g.

B.A. Thomsom et al, Adv. Mass Spectrom. 1980, 8B, pp. 1422–1428.

T. Sakuma et al, Chem. Anal. and Boil. Fate: Polynucl. Aromat. Hydrocarbons, Int. Symp. 5th, 1981, pp. 179–188.

M.E. Krzymien et al, Anal. Chim. Acta 1986, 190, 133–142.

H.R. Buser Anal. Chem. 1986, 58, 2913–2919.

C. Chiu et al, Chemosphere 1987, 16, 1625–1630.

S.N. Ketkar et al, Chem. Abstr. 1989, 110, abstract 44040g.

B.A. Eckenrode et al, Int. J. Mass Spectrom. Ion Processes 1990, 99, 151–167.

C. Moore et al, Rapid Commun. Mass Spectrom. 1990, 4, 418–420.

M.R. Nimlos et al, Environ. Sci. Technol. 1992, 26, 545–552.

J. Villinger et al, Organohalogen Compd. 1993, 11, 121–125.

J.F. Vicard et al, Fresenius J. Anal. Chem. 1994, 348, 101–105.

M.A. Dearth et al, J. Am. Soc. Mass Spectrom. 1994, 5, 1107–1114.

M. Lausevic et al, Rapid Commun. Mass Spectrom. 1995, 9, 927–936.

A. Bergman et al, Chemosphere 1995, 30, 1921–1938.

K. J. Hart et al, Rapid Commun. Mass Spectrom. 1996, 10, 352–360.

D. M. Chambers et al, Anal. Chem. 1997, 69, 3780–3790.

M. A. Dearth et al, Anal. Chem. 1997, 69, 5121–5129.

K. Mohr et al, Chemosphere 1998, 37, 2409–2424.

* cited by examiner

MAIN COMPONENTS INCLUDED IN FLUE GAS

FIG. 31A

| CHLORINE NUMBER | 2 | 3 | 4 | 5 | 6 |
|---|---|---|---|---|---|
| MOLECULAR WEIGHT | 146 | 180 | 214 | 248 | 282 |
| MONITORED MASS | 146 | 180 | 214, 216 | 250, 252 | 284, 286 |

FIG. 31B

| CHLORINE NUMBER | 2 | 3 | 4 | 5 | |
|---|---|---|---|---|---|
| MOLECULAR WEIGHT | 162 | 196 | 230 | 264 | |
| MONITORED MASS | 161 | 195 | 229, 231 | 265, 267 | |

FIG. 31C

| CHLORINE NUMBER | 4 | 5 | 6 | 7 | 8 |
|---|---|---|---|---|---|
| MOLECULAR WEIGHT | 320 | 354 | 388 | 422 | 456 |
| MONITORED MASS | 320, 322 | 356, 358 | 390, 392 | 424, 426 | 458, 460 |

CHEMICAL MONITORING METHOD AND APPARATUS, AND INCINERATOR

This is a continuation application of U.S. Ser. No. 09/447,577, filed Nov. 23, 1999, now abandoned. This application is related to U.S. Ser. No. 10/119,844, filed Apr. 11, 2002.

BACKGROUND OF THE INVENTION

This invention relates to a monitoring apparatus which measures the concentration of dioxins and related compounds such as dioxin precursors in flue gas or the atmosphere by detecting dioxins and related compounds present in combustion gases from incineration of domestic waste and industrial waste, gases from metal refineries, automobile exhaust or the atmosphere. It relates also to a combustion controller which efficiently employs the results of monitoring in combustion.

When waste is incinerated in a garbage incineration plant, highly toxic dioxins are produced in the flue gas. This gives rise to environmental pollution and is a serious social problem.

Dioxins are toxic to humans in various ways. Not only do they have acute toxicity, but they are also carcinogenic and teratogenic, and recently, it has been shown that they act as "environmental hormones", false hormones which disturb the internal secretions of the body. Dioxins are also known to be discharged in waste gases from metal refining, exhaust from automobiles, or lye from bleaching processes.

The term "dioxins" is a general term referring to 75 isomers of polychlorinated dibenzene paradioxin (PCDDS) and 135 isomers of polychlorinated dibenzofuran (PCDFs), and in the wider sense includes polybisphenyl chlorides (Coplanar PCBS). Hereafter, dioxin and related compounds will be referred to simply by the general term "dioxins".

Although a great deal is known about the mechanisms by which dioxins are produced ("Bunseki", 1998, pp. 512–519), the conditions under which this occurs vary widely depending on location and mechanism, and are very complex. One of the leading factors is considered to be reaction between carbon and chlorine (de novo or new product synthesis) due to metal chlorides of cobalt, iron and copper which are present in the ash of combustion processes under the high temperature of incineration plants, and which act as catalysts. In the basic reaction of this de novo synthesis, when carbon atoms, chlorine atoms and oxygen atoms are present together at high temperature, they produce many organochlorine compounds such as dioxins, chlorobenzene and chlorophenol by radical reactions. It is said that this chlorobenzene and chlorophenol are themselves precursors of, and give rise to, dioxins. Formation of dioxins in a waste incineration plant is said to mainly occur in two places, i.e., a process which takes place during incomplete combustion in an incinerator when the incineration temperature is less than 800° C., and in a de novo synthesis in a boiler or dust filter at a temperature of 250° C. to 550° C.

Various policies have been devised to reduce the formation of highly toxic dioxins in an incinerator plant as much as possible. To inhibit dioxin emission into the environment, techniques have been devised to improve incineration conditions and remove dioxin efficiently. However, much time and effort were needed to develop this inhibition technology. Specifically, garbage was incinerated under certain conditions, the concentration of dioxins in flue gas or ash under these conditions was determined, a correlation between combustion conditions and dioxin amount was found, and optimum incinerator conditions or dioxin removal conditions were then found from this correlation.

To make an accurate measurement of dioxin concentration, reference must be made to the regulatory law concerning the assay of dioxins. Generally, quantitative analysis of dioxins is carried out by the technique shown on pp. 441–444 of Pharmacia Vol. 34, No. 5 (1998). This is done by complex pre-processing to separate only desired components from a sample taken from an incinerator under fixed conditions, and performing qualitative and quantitative analysis using a costly, large-scale high resolution mass analyzing device (having a mass resolution of 10000 or more) installed in special equipment which does not release dioxins outside the system.

At the same time, many observation monitors are installed in various parts of an incinerator such as a garbage incinerator to control its operation while it is running. These include monitors for monitoring the temperature of various parts of the incinerator, an oxygen concentration monitor, a carbon monoxide monitor, a nitrogen oxide ($NO_x$) monitor, a sulfur oxide ($SO_x$) monitor, etc. These monitors are used for monitoring and controlling combustion, but they may also be used indirectly as monitors for reducing dioxins as stated on pp. 89–92 of Waste Incineration Technology (Ohm Co., 1995). Specifically, oxygen monitors, carbon monoxide monitors and temperature monitors are observed so that flue gases are completely burnt, and formation of dioxins is inhibited as far as possible.

To monitor the operation of an incinerator, an alternative method has been proposed wherein, instead of attempting to measure the concentration of dioxins directly which may be present in only very low concentrations, another substance present in relatively high concentration is measured, and the concentration of dioxins is estimated from the result. Examples of this technique and devices employing it are given in Yokohama National University Environmental Research Abstracts (Vol. 18, 1992), Japanese Patent Laid-Open No. Hei 4-161849, Japanese Patent Laid-Open No. Hei 5-312796, Japanese Patent Laid-Open No. Hei 7-155731, Japanese Patent Laid-Open No. Hei 9-015229, and Japanese Patent Laid-Open No. Hei 9-243601.

In the technique disclosed by Yokohama National University Research Abstracts (Vol. 18, 1992), Japanese Patent Laid-Open No. Hei 4-161849, and Japanese Patent Laid-Open No. Hei 5-312796, chlorobenzenes are measured by gas chromatography (GC), and are used as indicator for dioxins. The dioxins are estimated from the correlation between the two.

In the technique shown in Japanese Patent Laid-Open No. Hei 7-155731, dioxins in combustion ash are thermally decomposed by heat treatment of the ash, and dioxins are thereby inhibited. Chlorobenzenes or chlorophenols present in the ash before and after heating are analyzed, and a dioxin elimination factor is estimated. In this way, thermal decomposition conditions can be optimized.

In the technique shown in Japanese Patent Laid-Open No. Hei 9-015229, the concentrations of chlorobenzene and chlorophenol in flue gas are measured, and the dioxin concentration is found from this together with a dust concentration and flue gas retention time which are measured separately.

In the technique shown in Japanese Patent Laid-Open No. Hei 9-243601, chlorobenzenes and chlorophenols in flue gas are measured in real time, and the dioxin concentration is measured continuously. The concentrations of chlorobenzenes and chlorophenols are found by leading flue gas into a laser ionization mass spectrometer, ionizing the gas and performing a mass analysis. As a result, the dioxin concentration is found indirectly.

It was hoped that the formation of dioxins and their emission from garbage incineration plants would be reduced by these attempts to improve combustion conditions or use of eliminating techniques. However, it is necessary to measure, in real time, how much dioxin has actually been reduced by adoption of these curtailment policies. From this viewpoint, the following problems are inherent in the conventional methods mentioned above.

Although precise analytical results for dioxins, including types of isomers and their amount, can be obtained from the mandatory methods for its assay, the analysis itself is extremely complex. In addition, special equipment to avoid releasing dioxins outside the system and a costly, bulky, high resolution magnetic mass spectrometer are necessary, and skilled measurement techniques are required. Consequently, the analysis of dioxins cannot be conducted in the incineration plant "on site", which meant that ash samples or gas samples had to be sent to an analysis center, the analysis took almost a week, and the cost involved per sample was of the order of several hundred thousand yen.

There is very little correlation between the numerical values obtained by observation monitors currently employed to control the operation of garbage incinerators, such as oxygen monitors, carbon monoxide monitors, temperature monitors, nitrogen oxide ($NO_x$) monitors and sulfur oxide ($SO_x$) monitors, and the concentration of dioxins. Therefore, it was impossible to know whether or not emission of dioxins was being suppressed, or how much dioxins were being discharged, while an incinerator was operating. Hence, from these indirect monitors, even an estimate of dioxin concentration could not be obtained.

In the techniques indicated by Yokohama National University Environmental Research Abstracts (Vol. 18, 1992), Japanese Patent Laid-Open No. Hei 4-161849 and Japanese Patent Laid-Open No. Hei 5-312796, a minimum of 30 minutes to 1 hour is needed for measurement apart from trapping and concentration time. Moreover, it was difficult to selectively detect chlorobenzenes in the organic compounds which are present in large quantities in flue gas, and there was also a possibility of erroneous measurements due to interfering substances.

In the technique disclosed by Japanese Patent Laid-Open No. Hei 7-155731, specific techniques such as for as on-line sample introduction and automatic measurement are not described, and the measurement itself relied on conventional methods such as GC which required about 20 or 30 minutes per sample apart from the extraction operation.

In the technique disclosed by Japanese Patent Laid-Open No. Hei 9-015229, a clear basis is not given for the relation between dioxins, chlorophenols and chlorobenzenes which is assumed in the invention, and the determination of chlorobenzenes and chlorophenols was performed by the conventional methods which take time such as gas chromatography.

The technique shown in Japanese Patent Laid-Open No. Hei 9-243601 discloses the possibility of real-time concentration measurement of chlorobenzenes, but in this multiphoton ionization, there is said to be a decrease of sensitivity of from 1/7 to 1/10 for each additional chlorine atom substituted in the benzene nucleus. Trichlorobenzene is ionized with an efficiency of only about 1/100 of that of monochlorobenzene, i.e., it can be said that the sensitivity to trichlorobenzene is only 1/100 that of monochlorobenzene.

2,3,7,8tetrachlorodibenzene-p-dioxin (2,3,7,8-TCDD), which is known to be the most toxic dioxin, is a dioxin wherein four hydrogens at positions 2, 3, 7 and 8 are replaced by chlorine. Moreover, all other toxic dioxins are compounds substituted by four or more chlorine atoms. If this highly toxic dioxin is synthesized from chlorobenzenes and chlorophenols, a chlorobenzene or chlorophenol with two, three or more chlorine atoms must be the precursor material. However, in the multiphoton ionization described in this publication, it is difficult to efficiently ionize polysubstituted chlorine compounds. In other words, it was extremely difficult to measure organochlorine compounds such as chlorophenols at a concentration of 1000 $ng/Nm^3$ which are said to be present in incinerator flue gas.

SUMMARY OF THE INVENTION

In order to solve the above-mentioned problems, this invention provides a monitor equipped with a sampling system for sampling flue gas and the atmosphere, an ion source for ionizing trace compounds in the sample gas at atmospheric pressure or a pressure close to atmospheric pressure, a mass analyzing part for mass analysis of ions produced by this ion source and measuring its ion current, and a data processor for processing measured signals. As ions can be detected rapidly by mass analysis, monitoring can be performed in real-time.

In this monitor, the tendency of dioxins, chlorobenzenes and chlorophenols to form negative ions is fully exploited. First, sample gas containing hydrocarbon molecules from the incinerator is led to the ion source using a pipe which is heated to prevent adhesion. In this ion source, trace compounds in the sample gas are selectively ionized by a negative corona discharge under a predetermined pressure to form negative ions. These negative ions are analyzed by mass spectrometry, then a qualitative determination of the sample gas is performed from the mass numbers of the observed ions and a quantitative determination of the sample gas is performed from the ion amount. In atmospheric pressure chemical ionization, unlike the conventional laser ion method, the ionizing efficiency does not depend much on the number of chlorine atoms, so dioxins, or dioxin precursors (chlorobenzenes or chlorophenols) with different numbers of chlorine atoms can be detected with high sensitivity. This means that components such as dioxins or dioxin precursors can be monitored. Further, a negative ion is formed by deprotonation from the dioxin precursors in flue gas. This negative ion is introduced to a three-dimensional quadruple mass spectrometer to form a negative ion wherefrom one chlorine atom has been eliminated. The method makes it possible to predict the dioxin generation amount by selectively performing mass analysis on particular decomposition products from dioxin precursors in the negative ions which are produced.

Therefore, dioxins or dioxin precursors present at low concentrations in flue gas can be detected with high sensitivity and rapidity using an ion trap mass spectrometer which traps the ions using a high frequency electric field, and then performs mass analysis.

BRIEF DESCRIPTION OF THE DRAWINGS

FIGS. 31A, 31B and 31C are respectively diagrams showing detected ions.

DETAILED DESCRIPTION OF THE PREFERRED EMBODIMENTS

Embodiment 1

Figure 1:
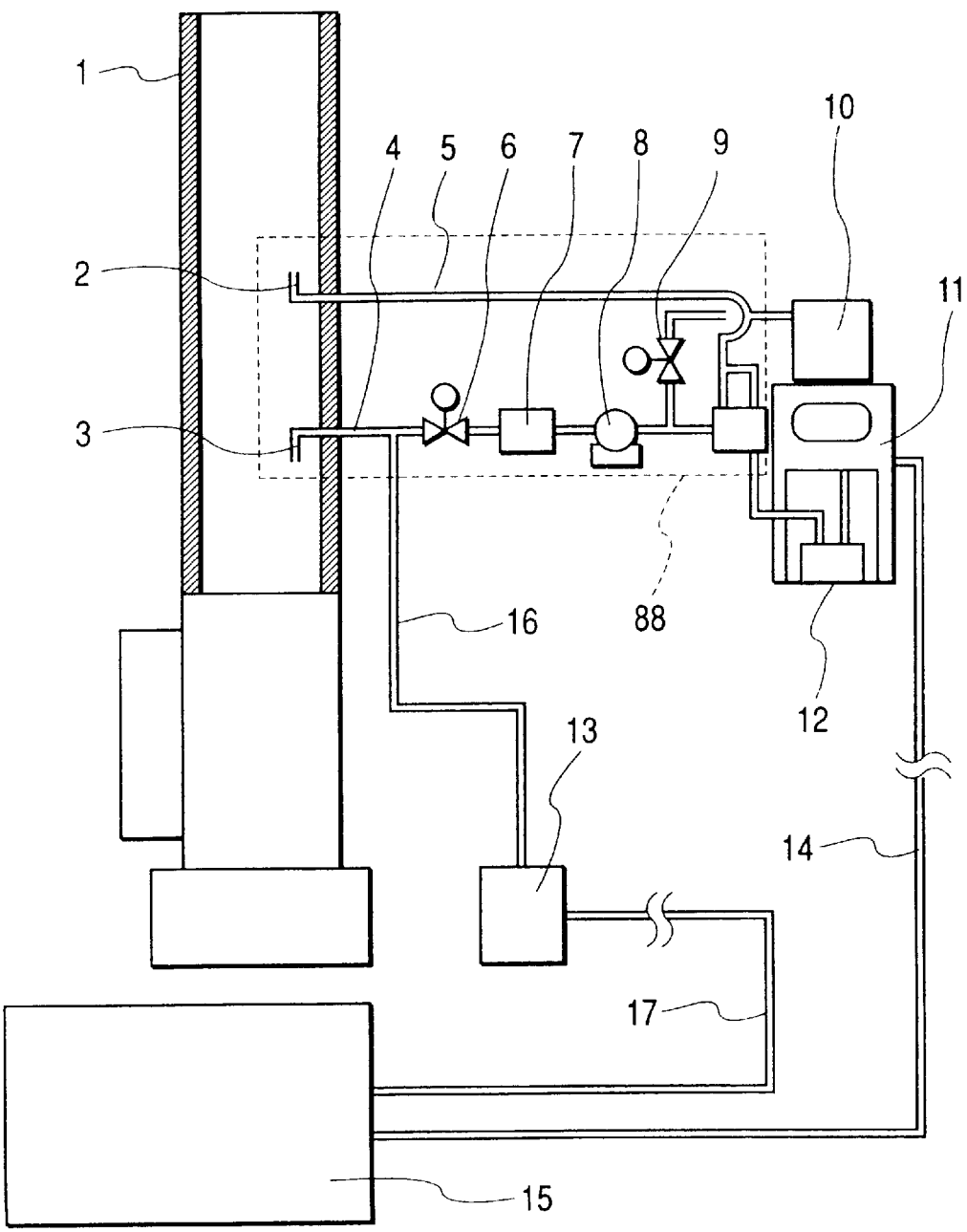
FIG. 1 is a diagram showing the construction of a flue, monitor and combustion controller.

FIG. 1 is a diagram showing the construction of a monitoring system according to one embodiment of this application. This system basically comprises a gas sampling unit 88 (inside the dotted line in FIG. 1) for sampling gas from a flue 1 which is to be measured, a monitor 11 for detecting substances to be measured in the sample gas, and a combustion controller 15 for utilizing the detection results in combustion control.

The sampling unit 88 comprises a gas sampling probe 3, sample gas pipe 4, change-over valve 6, filter 7, gas blow pump 8, waste gas pipe 5, and waste gas probe 2. As a whole, the sample gas introduction system has the function of sending sample gas to the monitor regularly without loss of substances to be measured due to adhesion and condensation, and at a fixed flowrate. For this purpose, although not illustrated, the whole of the sampling unit 88 is heated to from 100 degrees C. to about 300 degrees C. by a wire heater. This heating temperature varies with the substances to be measured. To keep the sampling unit warm, it is effective to surround the sample gas pipe 4, for example, with an insulating material. In the monitor 11, the substances to be measured are detected (monitored) by selectively and efficiently ionizing these substances in the sample gas introduced, and performing mass analysis of the ions produced in the mass analysis part.

The detected signal is sent to the data processing part where it is converted to a concentration from a calibration curve, and output to a CRT or printer as data. It is also sent to the combustion controller 15 as data for combustion control of the incineration plant via signal and control lines 14. Further, an instrument part 13 is provided comprising observation monitors such as an oxygen monitor, carbon monoxide monitor, temperature monitor, nitrogen oxide ($NO_x$) monitor, sulfur oxide (SOx) monitor and hydrogen chloride monitor, and combustion is controlled by the monitor 11 in view of the results obtained.

Figure 2:
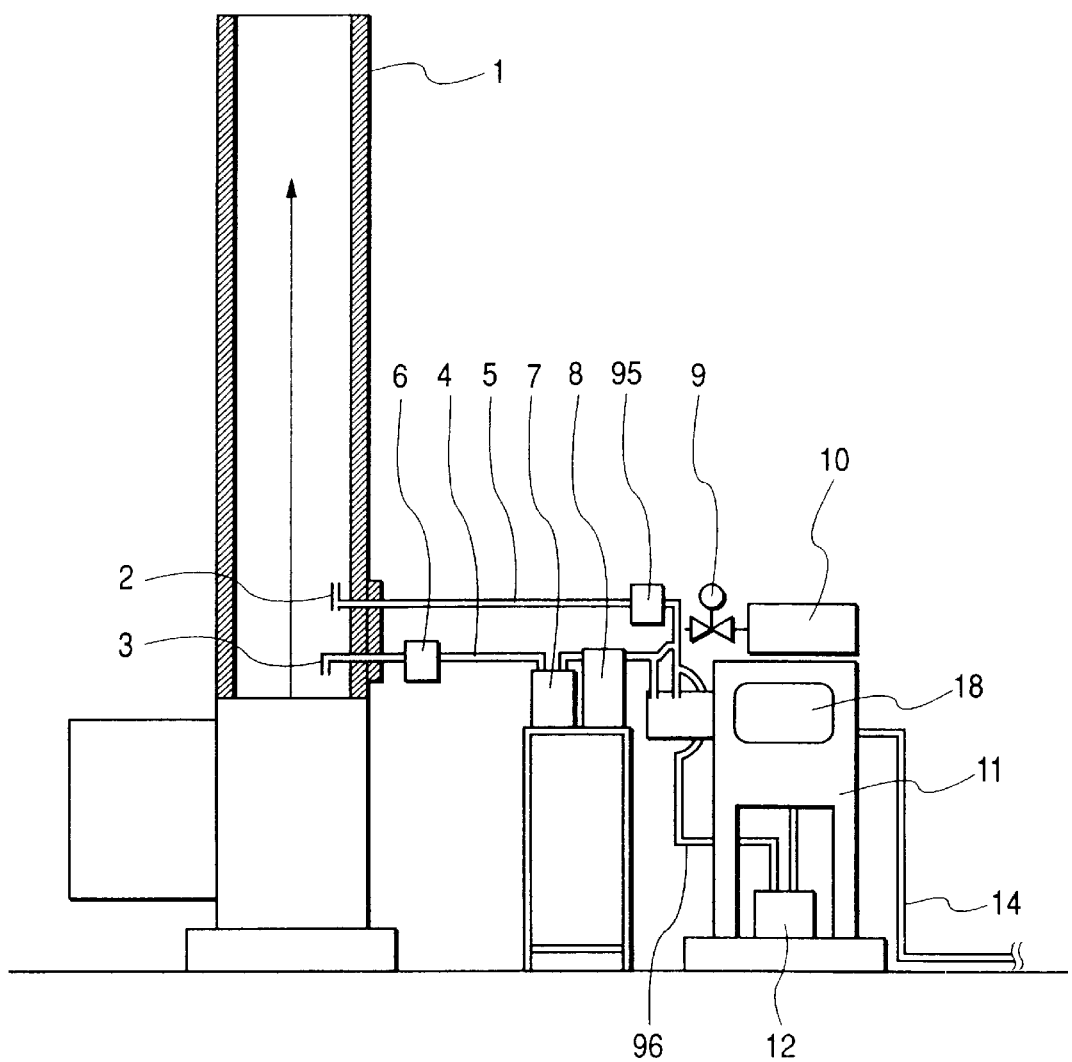
FIG. 2 is a diagram showing the construction of the flue and monitor.
Figure 3A:
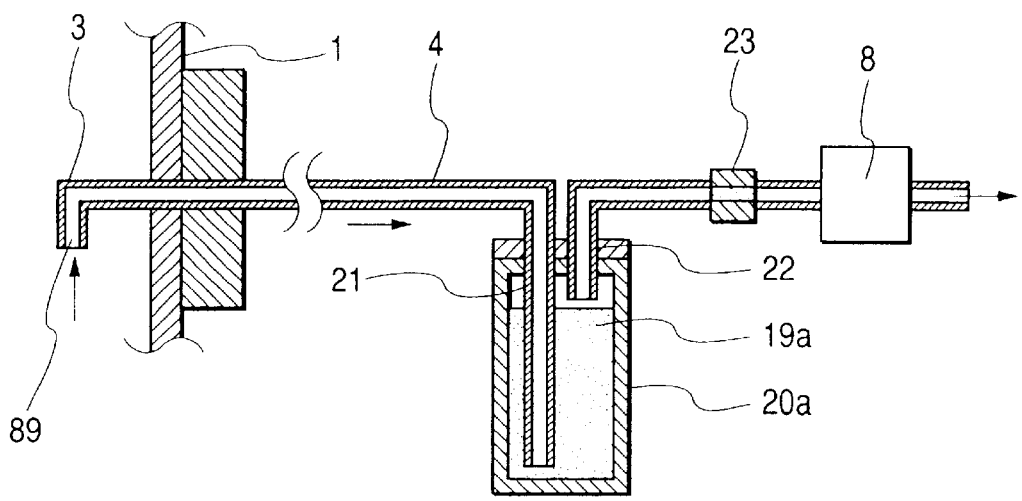
FIGS. 3A, 3B are diagrams showing the construction of a filter.
Figure 3B:
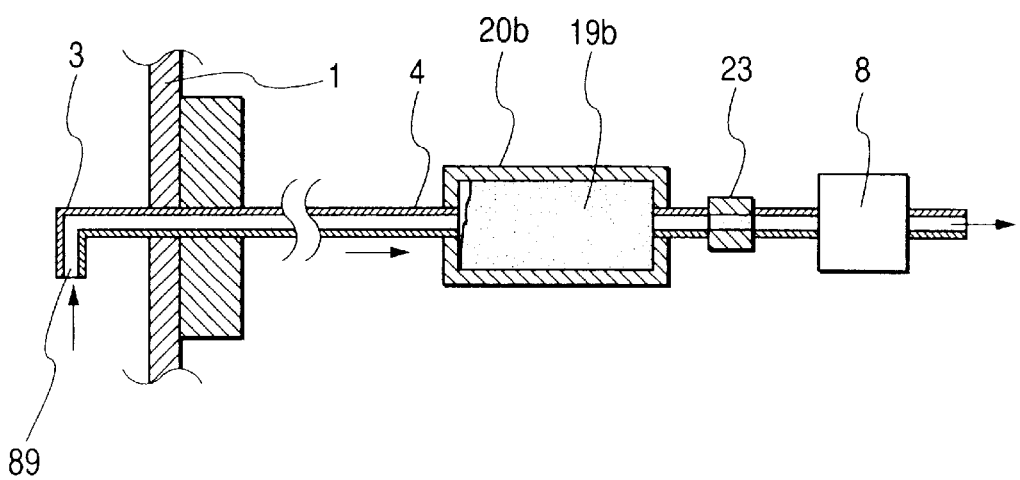

In FIGS. 2 and 3A, 3B, the gas sampling part 88 and monitor 11 are shown enlarged. When gas is sampled, the gas sampling probe 3 which has a sampling port 89 upstream of the flow of flue gas is inserted in the flue 1. A change-over valve 6 is provided after the gas sampling probe 3 to control the introduction of sample gas to the monitor 11. The sample gas pipe 4 is used to transport the sample gas, and this is heated to from 100 degrees C. to about 300 degrees C. by a wire heater, not shown, to prevent adsorption and condensation of the substances to be measured on the pipe wall. Temperature unevenness can be reduced by winding a heat insulating material around the whole piping. The bore of the sample gas pipe 4 depends on the flowrate of sample gas to be passed through it, but it is of the order of 1 mm to 100 mm.

The sample gas is introduced to the filter 7 where solid impurities and ash in the sample gas are removed. FIG. 3 shows an enlargement of the filter 7. The diagram shows a case where two kinds of filter, i.e., a dust filter 20 and metal filter 23, are provided midway along the sample gas pipe 4. In FIG. 3A, the dust filter 20a comprises a dust filter inlet pipe 21, a dust filter outlet pipe 22 and silica wool 19a packed in the dust filter. The tip of the dust filter inlet pipe 21 is led close to the base of the dust filter so that the sample gas is bound to come in contact with the silica wool 19a packed therein by the time the gas leaves the dust filter outlet pipe 22. The silica wool 19a is gradually contaminated by the gas, and is replaced when necessary. Also, a dust filter 20b filled with silica wool 19b may be arranged horizontally as in FIG. 3B, and if the construction is such that the interior may be observed, the state of contamination can be easily determined and the time when the silica wool should be replaced can be known.

To reduce adsorption of sample gas by the silica wool 19 in the dust filter 20 which does not easily transmit temperature, the wall surface temperature of the dust filter 20 must be raised above the temperature of the sample gas pipe 4. For example, when measuring dioxin precursors such as chlorobenzenes and chlorophenols, and the sample gas pipe 4 is at about 120 degrees C., it is effective to increase the temperature of the dust filter 20 to about 180 to 200 degrees C. Many solid impurities, ash, etc. can be removed by the dust filter 20, but if a metal filter 23 is provided thereafter, influx of still finer dust to the monitor 11 can be prevented. The size of the dust removed may be controlled by the mesh of the metal filter, and is often of the order of several micrometers. This part is also replaceable. Depending on the amount of solid impurities or ash at the gas sampling points, two or three of these filters may be combined. In such a case, prolonged monitoring is possible if the mesh of the filters is arranged to be progressively finer from upstream to downstream of the gas sampling points in the pipe. To prevent corrosion by flue gas, it is desirable that pipes and valves are made from stainless steel or titanium which do not easily corrode. To prevent components present in very small amounts from adsorbing to the wall surface of the piping, it is desirable to use a polytetrachloroethylene lined pipe or a glass lined pipe. Instead of a glass lined pipe, piping may be packed with glass tubes or quartz tubes cut to short lengths. A wide bore fused silica column used as a gas chromatography (GC) column may also be employed.

It is convenient if the aforesaid sample gas preprocessing part is provided with plural lines which can be changed over. That is, when one of the dust filters 20 is clogged with ash, etc., the line can be changed over to another of the filters 20, and the filter clogged with ash cleaned while measurements are continued.

Sample gas is introduced into the monitor 11 by the gas blow pump 8. The flowrate of sample gas introduced depends on the bore and length of the sample gas pipe, and the blowing speed of the pump 8, but it is of the order of 1–300 liter/minute. A mechanical pump such as a diaphragm pump may be used for the pump 8, but it is important to be able to heat the parts in contact with sample gas to some extent to prevent adsorption of the sample in the pump parts. Dioxin and its related compounds exist in flue gas only in minute amounts. These compounds are easily adsorbed to the wall surface of sampling systems such as pipes and filters, etc. To prevent this adsorption as much as possible, therefore, the whole sampling system is heated as mentioned above, or pipes are made of materials with low adsorption. Adsorption can be reduced if the amount of flue gas flowing in the piping is increased. That is, the residence time of flue gas in the piping is shortened as much as possible.

Moreover, when there is a difference in the sample gas amount flowing through the pipe 4 and an optimum sample gas amount which should flow into the monitor 11, a branch valve 9 may be formed as shown in FIG. 1 to control the gas amount flowing into the monitor 11.

Figure 4:
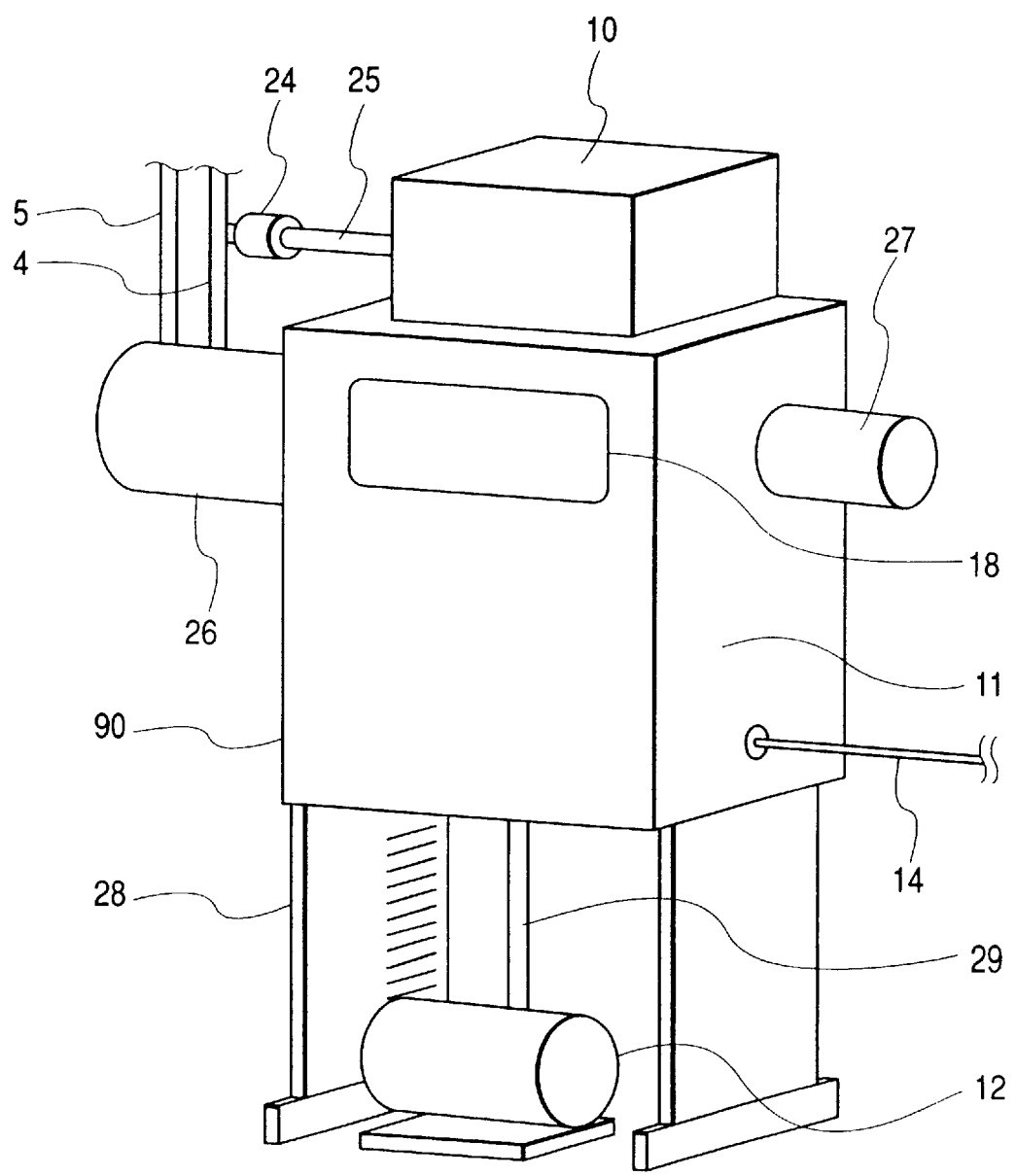
FIG. 4 is a diagram showing the external appearance of the monitor.
Figure 5:
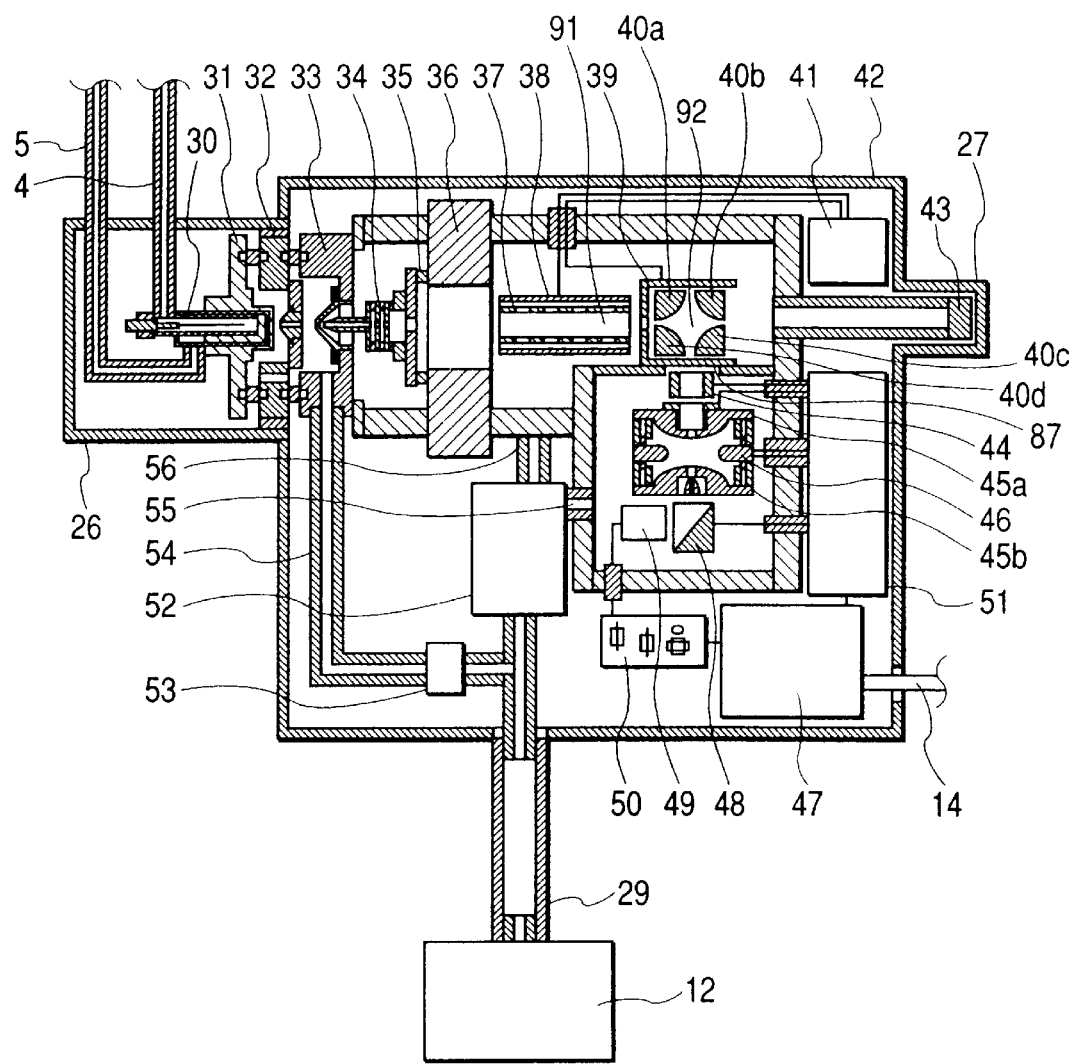
FIG. 5 is a diagram showing a typical construction of the monitor interior.

Next, the sample gas is introduced into the monitor 11. FIG. 4 and FIG. 5 respectively show the external appearance of the monitor 11 and the detail of the interior of the monitor 11. In order to install the analysis mainframe of the monitor 11 outdoors near the flue, it is placed in a well-sealed monitor rack 90 whereof temperature control is performed to some extent (approximately 10 to 50 degrees C.). The monitor rack 90 is fixed by a monitor support 28. An atmospheric pressure chemical ionization ion source housing 26 for ionizing the sample gas is installed in such a way that it can be easily dismantled to facilitate periodic cleaning of the ion source. Also, as will be described later, it is preferable to place a vacuum pump 12 which radiates a large amount of heat outside the monitor rack 90, as shown in FIG. 4. As mentioned above, the filter 7 is installed midway along the sample gas pipe 4, but in view of fine dust which has passed through it flowing into the interior of the mass analysis part, it is preferable to provide a dust filter housing 27 in a vacuum tank. The data measured by the monitor 11 are transmitted to the combustion controller 15 via the signal and control line 14.

An arrangement may be made so that the results on the CRT or printer may also be observed on the monitor 11 via an observation window 18 of the monitor. Also, by providing a standard sample generator 10, periodic inspection of monitor performance can be made via a standard sample change-over valve 24 and a standard sample pipe 25. That is, a standard gas is periodically introduced instead of flue gas, and it is confirmed whether or not ions from the standard gas are observed to be equal to or greater than a fixed amount. If the ion intensity observed is below the fixed amount, maintenance is performed.

Figure 7:
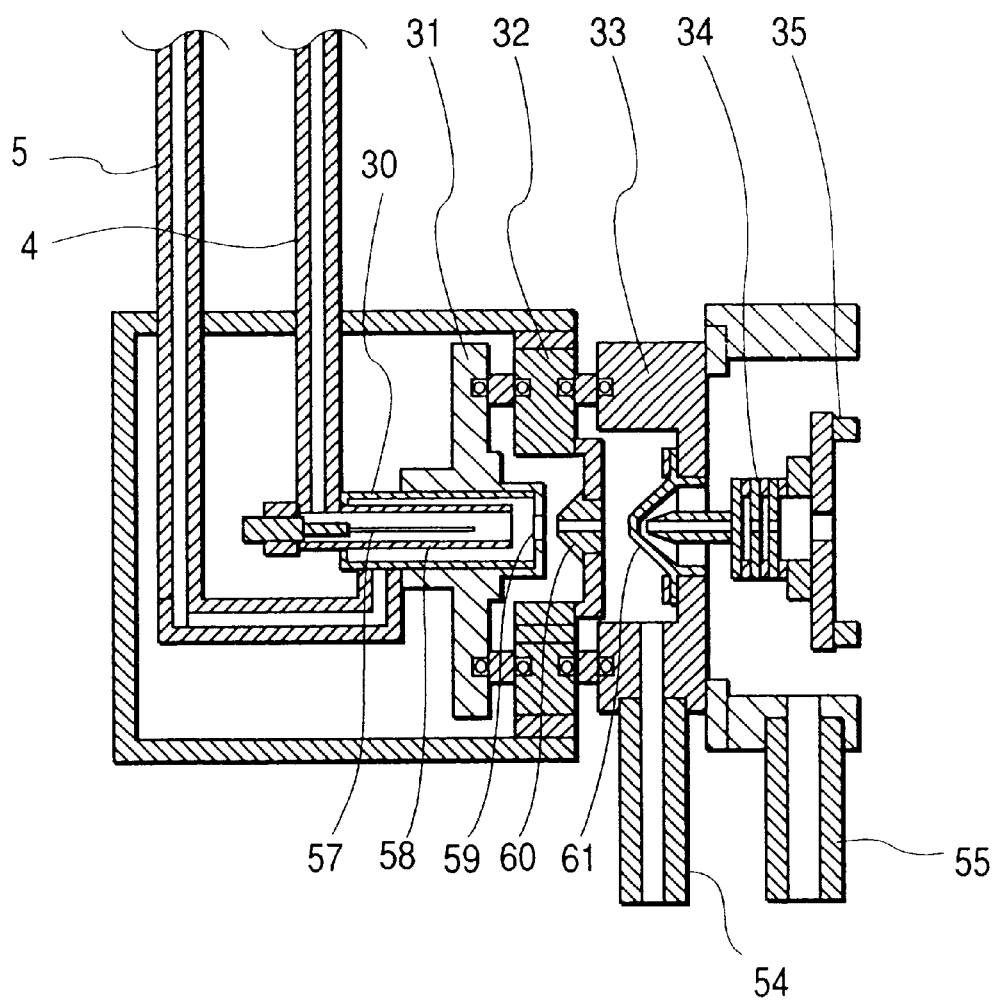
FIG. 7 is a diagram showing a typical construction of an ion source.
Figure 10:
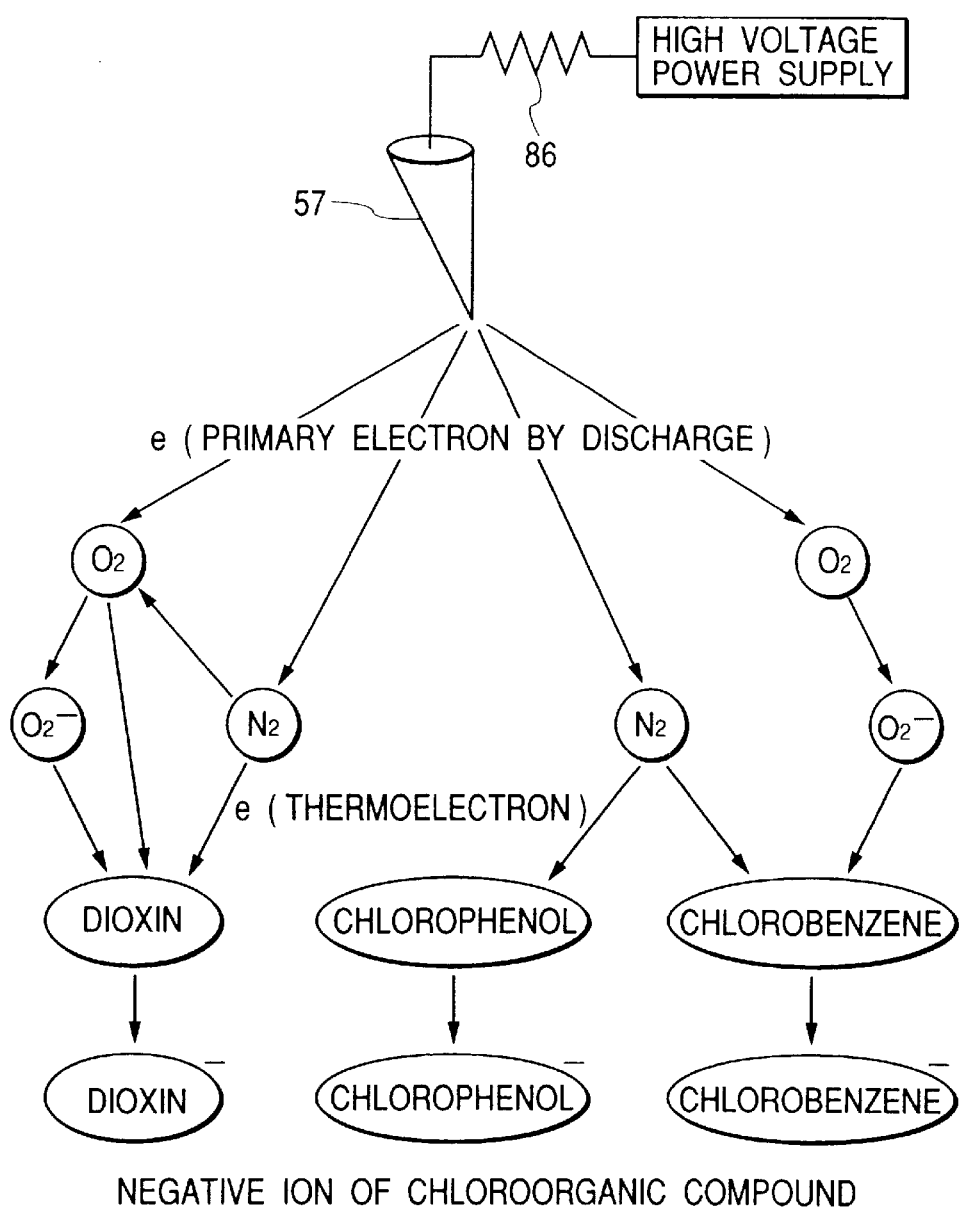
FIG. 10 is a diagram showing a corona discharge ion generation process.

The sample gas is then sent to a atmospheric pressure chemical ionization ion source 30 shown in FIG. 5. FIG. 7 shows an enlargement of the ion source 30. A high voltage (from about −3 kV to −7 kV) is applied to a corona discharge needle electrode 57 in a discharge counter electrode 58. The temperature of this area is kept at approximately 50 to 300 degrees C. by a heater, not shown. The distance between the corona discharge needle electrode 57 and discharge counter electrode 58 is about 1 to 10 mm. Due to the negative corona discharge at the tip of the needle electrode as a result of applying the high voltage, ionization of dioxins and dioxin precursors takes place. The details of this ionization due to the negative corona discharge may be described as follows. Dioxins and related substances have elements with high electronegativity in the molecule, such as a large number of chlorine atoms, oxygen atoms, etc., (Group VI and Group VII of Periodic Table). That is, they are organochlorine compounds. A toxic dioxin is a dioxin having from four to eight chlorine substitutions. These compounds easily trap low energy thermoelectrons to become negative ions. On the other hand, there is no ionization process wherein hydrocarbons which occur in large quantities in flue gas trap thermoelectrons to become negative ions. Therefore, even if hydrocarbon molecules are present in large quantities in sample gas, they do not become negative ions. Thermoelectrons can be produced in large quantities by corona discharge in the atmosphere, as shown in FIG. 10, and if a negative high voltage (approximately −3 kV to −7 kV) is applied to the needle-like corona discharge electrode 57, a corona discharge will start at the tip of the corona discharge electrode 57. Specifically, primary electrons due to this corona discharge are emitted from the tip of the corona discharge electrode 57. These primary electrons due to corona discharge are accelerated by the high voltage applied to the discharge electrode, and collide with surrounding atmospheric molecules (nitrogen and oxygen) to give rise to large numbers of secondary and tertiary electrons. These secondary, tertiary and quartenary electrons then suffer repeated elastic collisions with neutral molecules, so their energy gradually decreases, and they finally attain a resonance capture energy (2 eV or less). Consequently, the thermoelectrons which are produced in large amounts around the corona discharge electrode 57, are selectively captured by organochlorine compounds, such as dioxins, chlorobenzenes and chlorophenols. Oxygen captures a thermoelectron to form a $O_2^-$ ion. This ion collides with a dioxin or related compound, supplies a charge to an organochlorine compound which more easily becomes a negative ion, or reacts with an organochlorine compound to form these negative ions. Therefore, even if oxygen is present in flue gas or the atmosphere to a concentration of 100 ppm or more, it does not interfere with the formation of negative ions. In an atmospheric pressure ionization process, water forms an $OH^-$ ion. This $OH^-$ ion collides with a dioxin or an organochlorine compound, and the negative charge is transferred to the dioxin or organochlorine compound, or withdraws a proton ($H^+$) from a neutral molecule to form a negative ion. Hence, there is a considerable advantage in using a negative corona discharge for ionizing organochlorine compounds, such as dioxins, chlorobenzenes and chlorophenols.

Figure 9:
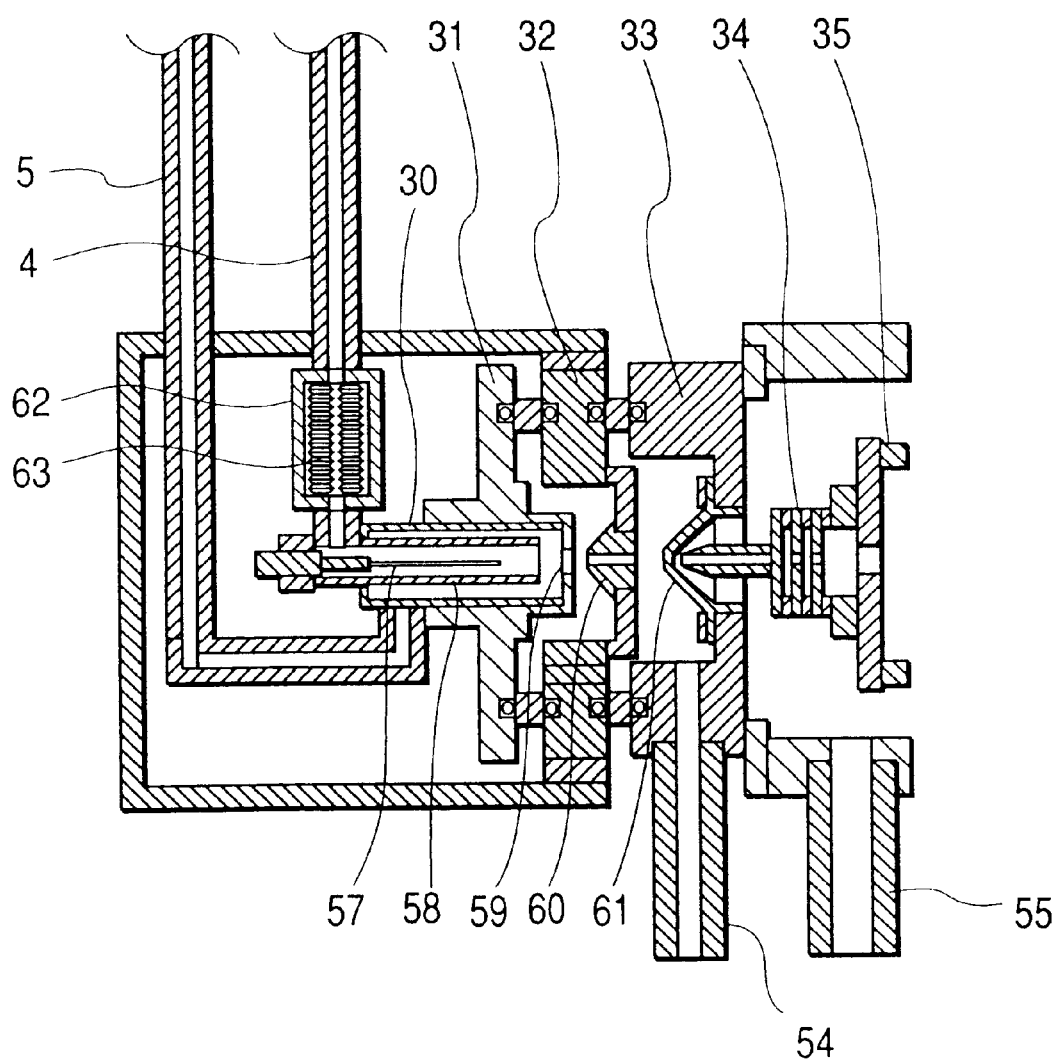
FIG. 9 is a diagram showing yet another construction of the ion source.
Figure 20:
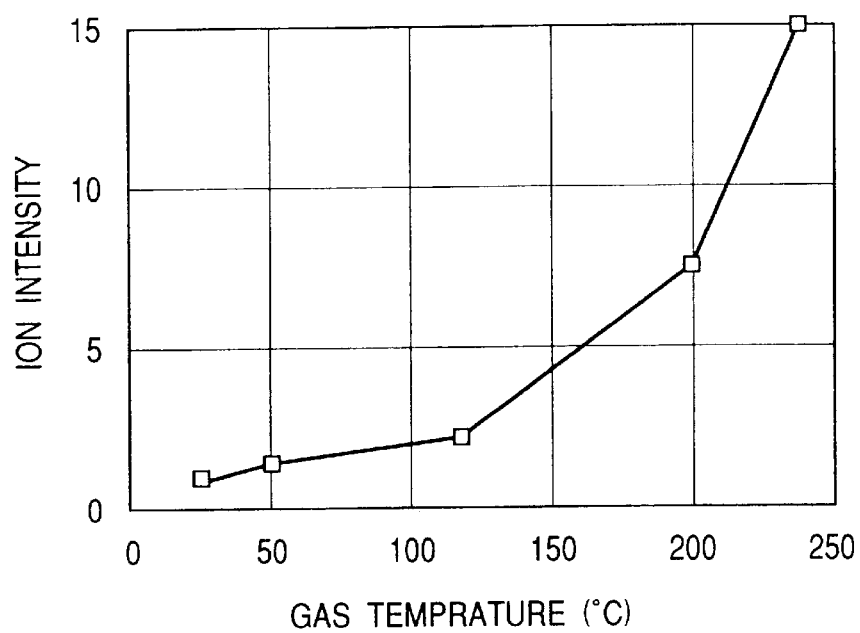
FIG. 20 is a diagram showing a relation between gas temperature and ion intensity in an atmospheric pressure ion source.
Figure 21:
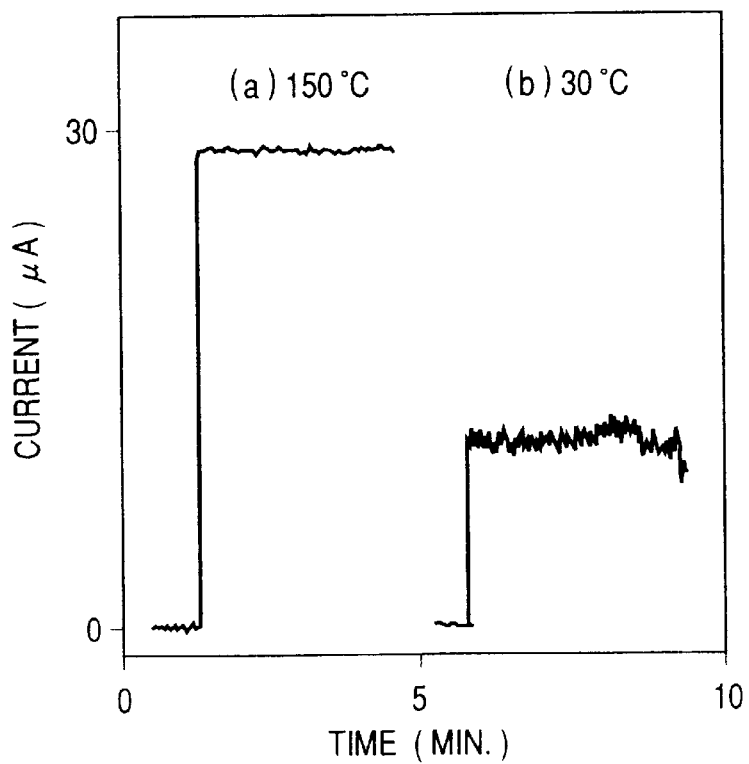
FIG. 21 is a diagram showing a relation between gas temperature and ion current in the atmospheric pressure ion source.

Water molecules which are present in large amounts in flue gas collide with the negative ions produced, and plural water molecules bond with the negative ions to form cluster ions. If the mass of a naked ion is M, and if the number of added water molecules is n, the mass of this cluster ion will be (M+18n). 18 is the molecular weight of water. The formation of cluster ions not only interferes with the analysis, but makes a high sensitivity measurement impossible. The formation of these cluster ions is promoted by cooling the molecules or ions, therefore an effective means of suppressing cluster ions is to maintain the ion source 30 at from about 50 to 500 degrees C., and preferably in the range of from about 100 to 300 degrees C. Heating may be performed by providing a heater to each part, or by providing a sample gas heater unit 62 and heating the sample gas directly by a heater 63 comprising multiple coils of metal wire wound therein, as shown in FIG. 9. The importance of this may also be seen from the data shown in FIGS. 20 and 21. FIG. 20 shows the relation of the temperature of the sample gas to the ion intensity obtained when the gas is heated by the sample gas heater unit 62. It is seen that when the gas temperature rises, the ion intensity rises abruptly, the variation above 100 degrees C. being particularly remarkable. FIG. 21 shows the difference of ion intensity obtained when the temperature of the gaseous sample is (a) 150 degrees C. and (b) 30 degrees C. It is seen that when heating is performed, the current increases by about 2.5 times compared to the case where heating is not performed for the same corona discharge voltage (−2.5 kV). Current stability is also much better when heating is performed. If the sample gas is at high temperature, for example, if it has reached 100 degrees C. or more, the moisture in the gaseous sample introduced will also evaporate and ionization by corona discharge will proceed efficiently and stably.

The details of the mass analysis part, etc., will now be described using FIGS. 5 and 7. Mass spectrometers of various kinds can be used in analyzing the ions which are produced, but below, the case is described where an ion accumulating type ion trap mass spectrometer is used. The situation is the same when a quadruple mass spectrometer which performs a mass separation using the same high frequency electric field, and a magnetic field type mass spectrometer using mass variance in a magnetic field, are employed.

Figure 8:
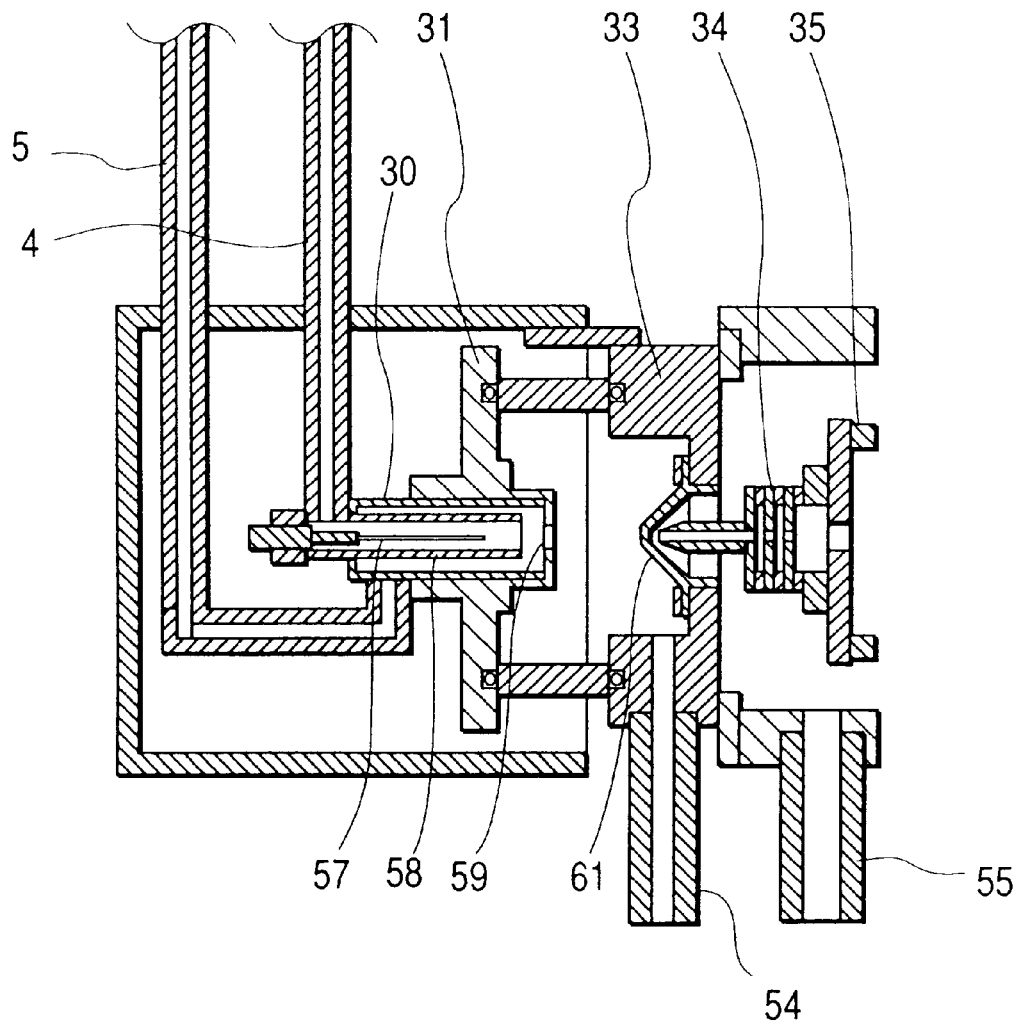
FIG. 8 is a diagram showing another construction of the ion source.

The negative ions produced by the corona discharge at the tip of the corona discharge needle electrode 57 pass through a first aperture 59 (diameter approximately 0.3 mm, length approximately 0.5 mm) in a first flange 31 of a differential pumping region, a second aperture 60 (diameter approximately 0.3 mm, length approximately 0.5 mm) in a second flange 32 and a third aperture 61 (diameter approximately 0.3 mm, length approximately 0.5 mm) in a third flange 33 which are heated by a heater, not shown. These apertures are heated by the heater to about 100 to 200 degrees C. A voltage is applied between the first aperture 59 and second aperture 60, and between the second aperture 60 and third aperture 61, which increases ion transmission efficiency. At the same time, cluster ions formed by adiabatic expansion are declustered due to collision with remaining molecules so as to produce ions of the sample molecules. The differential pumping region is usually evacuated by a robust pump such as a rotary pump, scroll pump or a mechanical booster pump. A turbomolecular pump may also be used to evacuate this area. The pressure between the second aperture 60 and the third aperture 61 is in the range of 0.1 to 10 Torr. It is also possible to construct the differential pumping region using two apertures, i.e., the first aperture 59 and third aperture 61, as shown in FIG. 8. However, as the gas amount flowing in increases as compared with the above-mentioned case, the evacuation rate of the vacuum pump used must be increased and the distance between the holes must be increased. In this case also, it is important to apply a voltage between the two apertures.

Figure 14A:
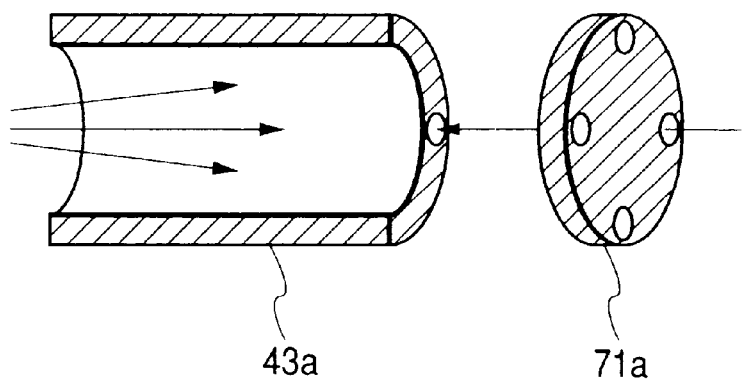
FIGS. 14A, 14B are diagrams showing constructions of a dust filter.
Figure 14B:
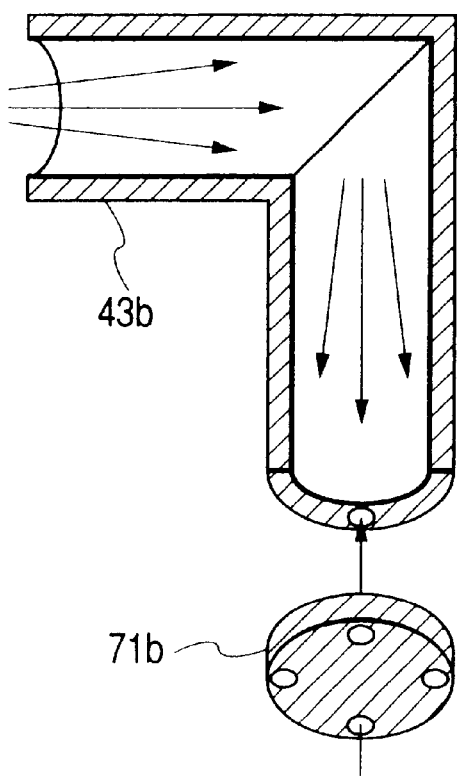

After the ions so produced have passed through the third aperture 61, they are focused by a focusing lens 34. An Einzel lens comprising three electrodes is usually used for this focusing lens 34. The ions then pass through an electrode 35 with a slit. Due to the focusing lens 34, the ion which have passed through the third aperture 61 are focused on this slit. Dust which is not focused collides with this slit part and seldom enters the mass analysis part. After the ions have passed through the electrode 35 with the slit, they pass through a gate valve 36, are again focused by a double cylinder type focusing lens 91 comprising an inner cylindrical electrode 37 and outer cylindrical electrode 38 having a large number of openings, and are deflected by about 90degrees by a deflector 92 comprising deflector electrodes 40*a, b, c, d* (a cylindrical electrode split into four parts) situated inside a screening electrode 39 to eliminate the effect of external voltages. In the double cylinder type focusing lens 91, the ions are focused using the electric field of the outer cylindrical electrode 38 which spreads out from the openings of the inner cylindrical electrode 37. The reason why the ions are deflected at about 90 degrees is so that only ions are introduced into the mass analysis part, dust or other particles flowing into the vacuum from the third aperture 61 being ejected straight ahead to accumulate in a dust filter 43 in a vacuum tank. The dust filter 43 in the vacuum chamber may be (a) a cylindrical type or (b) a 90° curved type as shown in FIGS. 14A, 14B. In the case of the curved type, when dust accumulates at the bottom, cleaning may be easily performed by removing the flange 71*b*.

Figure 6:
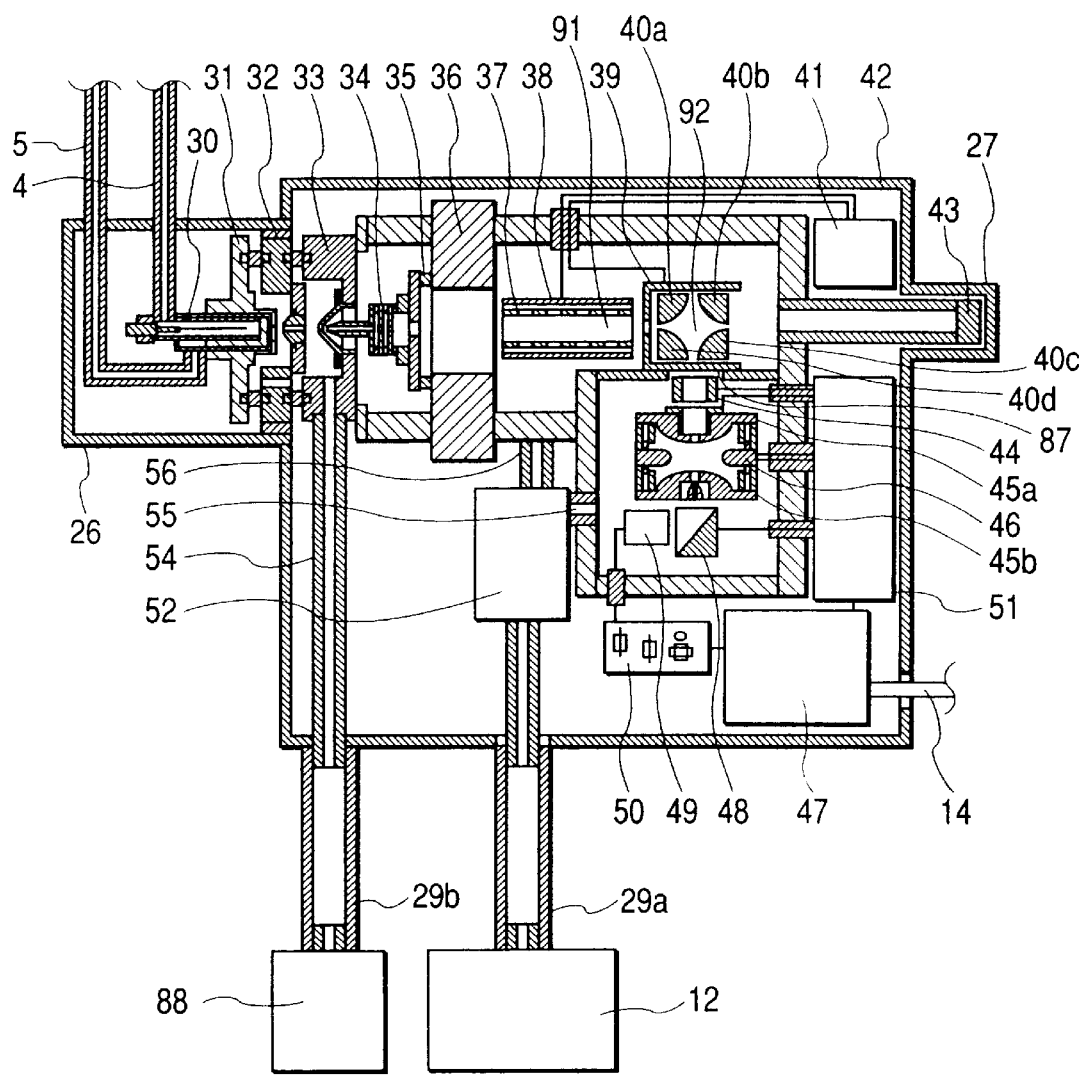
FIG. 6 is a diagram showing another construction of the monitor interior.
Figure 11:
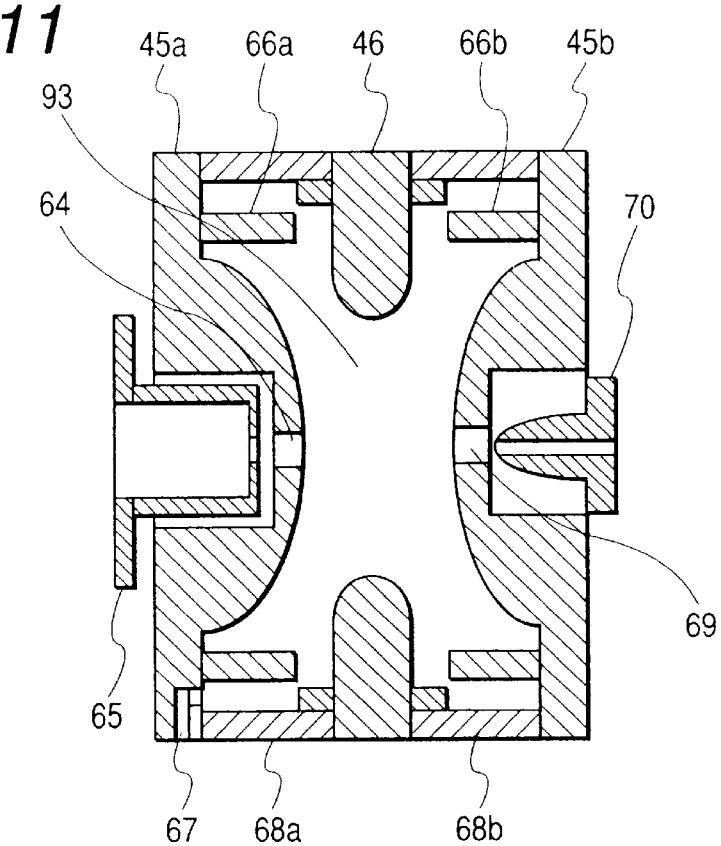
FIG. 11 is a diagram showing the construction of an ion trap mass analyzing part.
Figure 13A:
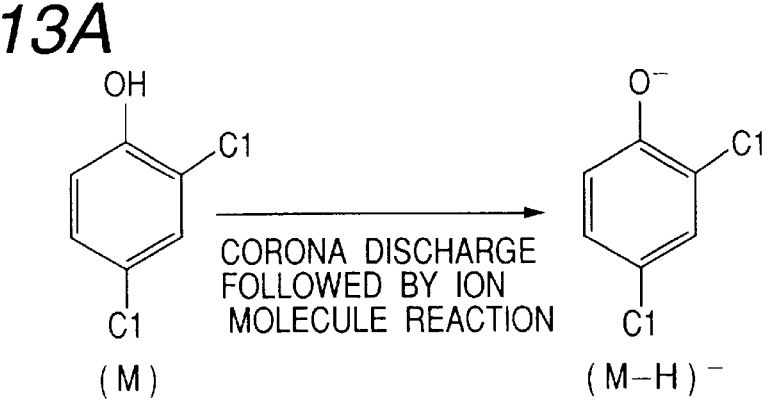
FIGS. 13A, 13B are diagrams showing an ion generation process.
Figure 13B:
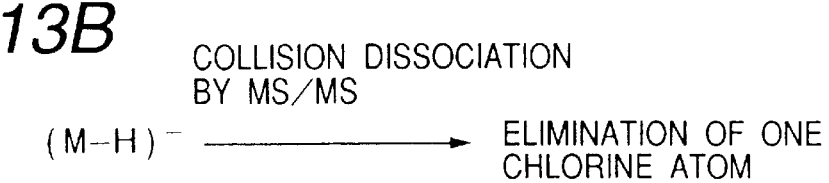
Figure 12:
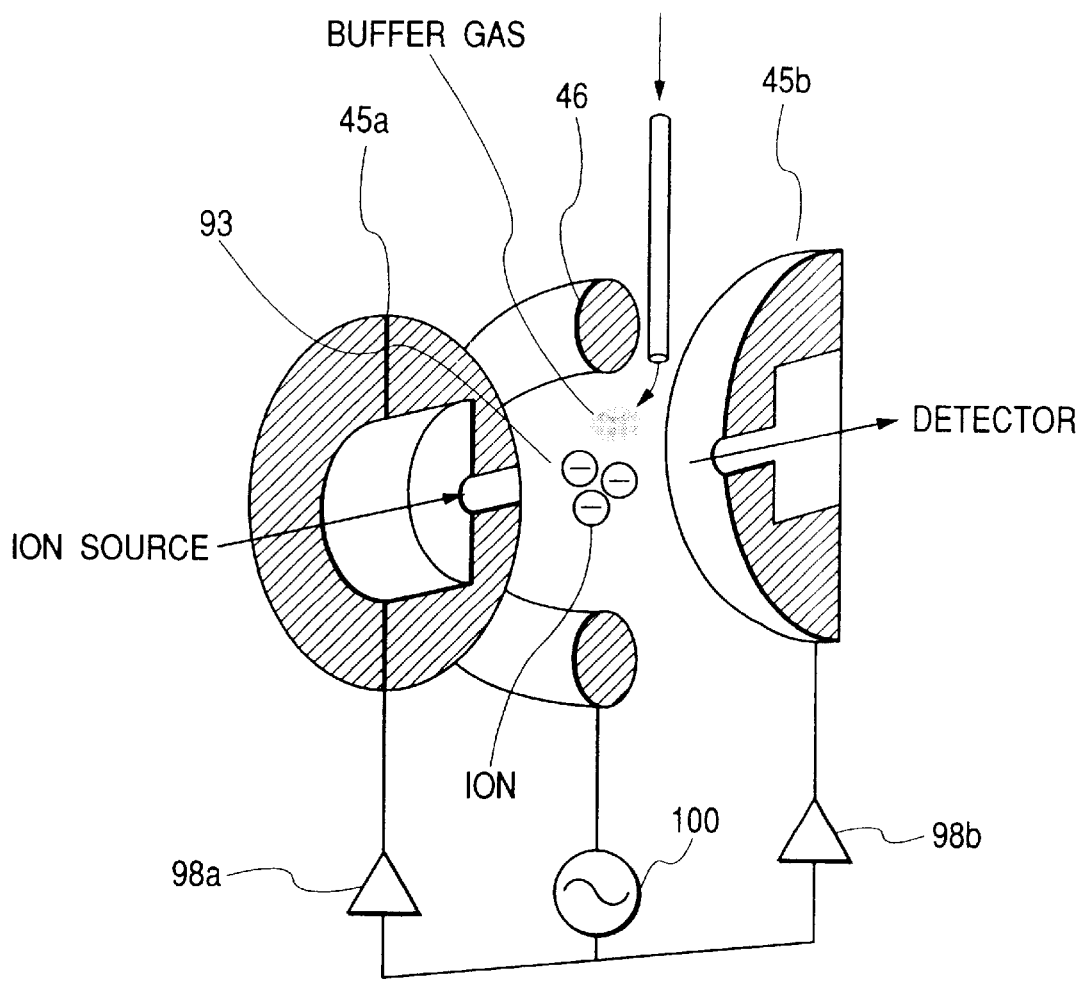
FIG. 12 is a diagram describing the construction of the ion trap mass analyzing part.

After the ions which pass through the deflector 92 are focused by a cylindrical electrode 44, they are introduced into an ion trap mass analyzing part 93. FIG. 11 shows an enlargement of the ion trap mass analyzing part 93 comprising a gate electrode 65, endcap electrodes 45*a, b*, a ring electrode 46, collar electrodes 66*a, b*, insulating rings 68*a, b*, and an ion extracting lens 70. The gate electrode 65 has the function of preventing ions outside from entering the ion trap mass analyzing part 93 when ions trapped in the mass analyzing part are removed from the system. As shown in FIG. 12, ions introduced to the mass analyzing part 93 collide with a buffer gas such as helium introduced into the mass analyzing part 93, and their orbit becomes small. They are then ejected from the system, each mass number in turn, by scanning with a high frequency voltage applied by a high frequency power supply 100 between the endcap electrodes 45*a, b* and the ring electrode 46, and pass through the ion extracting lens 70 to be detected by an ion detector 94. The pressure in the mass analyzing part 93 when the buffer gas is introduced is of the order of $10^{-3}$ to $10^{-4}$ Torr. The mass analyzing part 93 is controlled by a mass analyzing part controller 51 (FIGS. 5 and 6). One of the advantages of an ion trap mass spectrometer is that it has the ability to trap ions, and it can therefore detect ions even at low sample concentrations if the accumulating time is made longer. Therefore, even if the sample concentration is low, ions can be concentrated by a high factor in the mass analyzing part 93, and this very much simplifies sample preprocessing, e.g. concentration.

If the magnitude of the high frequency voltage applied by the high frequency power supply 100 between the endcap electrodes 45a, b and the ring electrodes 46 is set to a certain value while introducing ions into the mass analyzing part 93, a cut-off (low mass ion cutoff) of the ion mass numbers trapped between the endcap electrodes 45a, b and the ring electrode 46 can be achieved. This means that ions smaller than a certain mass are not trapped within the electrodes. In the low mass number region below 100, there are large numbers of ions derived from water, hydrogen chloride, $NO_x$, $SO_x$, etc. If these ions are not trapped in the endcap electrodes 45a, b band the ring electrode 46, saturation of ions in the electrodes can be prevented, and dioxins or organochlorine compounds which have large mass numbers can be efficiently trapped in the electrodes, as shown in FIGS. 31A to 31C. Further, unnecessary ions with large mass can be eliminated from the electrode by controlling the frequency of an auxiliary alternating voltage applied between the endcap electrodes 45a, b from auxiliary alternating current power supplies 98a, 98b shown in FIG. 12. In practice, a white noise auxiliary alternating current which does not contain the resonant frequency of the ions to be trapped by the mass analyzing part 93 is applied to the endcap electrodes 45a, b. The mass analyzing part 93 traps and accumulates only ions of target mass within the electrodes. Therefore, target molecular ions and fragment ions are efficiently accumulated and detected. In addition to the selectivity of the atmospheric pressure chemical ionization method, the further improvement of selectivity and sensitivity provided by the ion trap mass spectrometer makes it possible to detect organochlorine compounds including dioxins.

In the detection of ions extracted from the mass analyzing part 93, the ions are converted to electrons by a conversion dynode 48, and these electrons are detected by a scintillation counter 49, as shown in FIGS. 5 and 6. The signal obtained is amplified by an amplifier 50, and sent to a data processor 47.

A chamber containing the focusing lens 34, the electrode with a slit 35, the double cylinder type focusing lens 91, the deflector 92, the cylindrical electrode 44, the mass analyzing part 93 and the ion detector 94 as shown in FIGS. 5 and 6, is evacuated to approximately $10^{-4}$ to $10^{-6}$ Torr (at a rate of about 50 to 200 liter/second on the side of a second differential pumping region evacuation pipe 55 and a rate of about 50 to 150 liter/second on the side of a third differential pumping region evacuation pipe 56) by a split flow type turbomolecular pump 52.

In this regard, it is convenient to split the vacuum chamber after the gate valve 36 into two parts at the deflector 92, and evacuate the chamber split into two via the second differential pumping region evacuation pipe 55 and third differential pumping region evacuation pipe 56 using one split flow type turbomolecular pump 52, as shown in FIG. 5. This is convenient for the following reasons. Firstly, the mass analyzing part 93 is not easily contaminated by dust, etc. In addition, when the gate valve 36 is closed, the first to third apertures 61 are set at atmospheric pressure and the ion source 30 and differential pumping region are cleaned, the ion trap mass analyzing part 93 can be kept under vacuum, so the monitor 11 can be rapidly reinstated within about 1 or 2 hours after cleaning. The auxiliary vacuum pump 12 must be provided to the turbomolecular pump 52 on the back pressure side. This may be used in conjunction with the pump used for the differential pumping region, in which case a valve 53 is provided midway in a first differential pumping region evacuation pipe 54. In this embodiment, a scroll pump with a evacuation rate of approximately 500 liter/minute is used as the auxiliary vacuum pump 12. Further, a robust vacuum pump connected to the first differential pumping region evacuation pipe 54 can be made separate from the auxiliary vacuum pump 12 of the turbomolecular pump 52 via vacuum evacuation pipes 29a, b as shown in FIG. 6. In this case, a pump with a small evacuation rate of approximately 100 liter/minute may be used as the auxiliary vacuum pump 12 of the turbomolecular pump 52. In both of the cases shown in FIGS. 5 and 6, the use of this type of arrangement simplifies the vacuum pumping system of the atmospheric pressure chemical ionization mass spectrometer which tends to be very complex. In the examples of FIGS. 5 and 6, the case was shown of three stage differential pumping region, but if the gas flowrate in the first to third apertures 61 is suppressed, a two stage differential pumping system may also be used.

Figure 24:
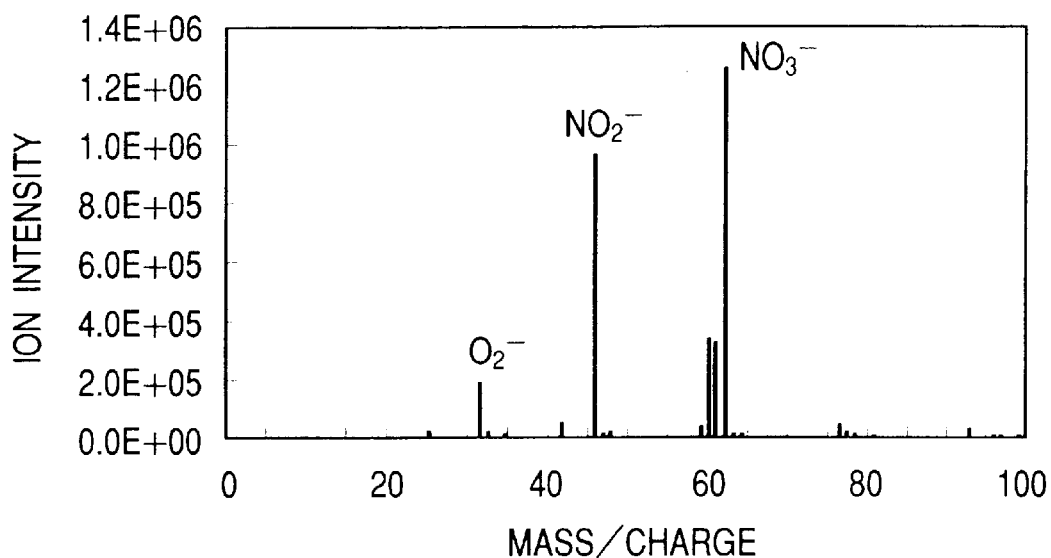
FIG. 24 is a diagram showing a typical mass spectrum.
Figure 25:
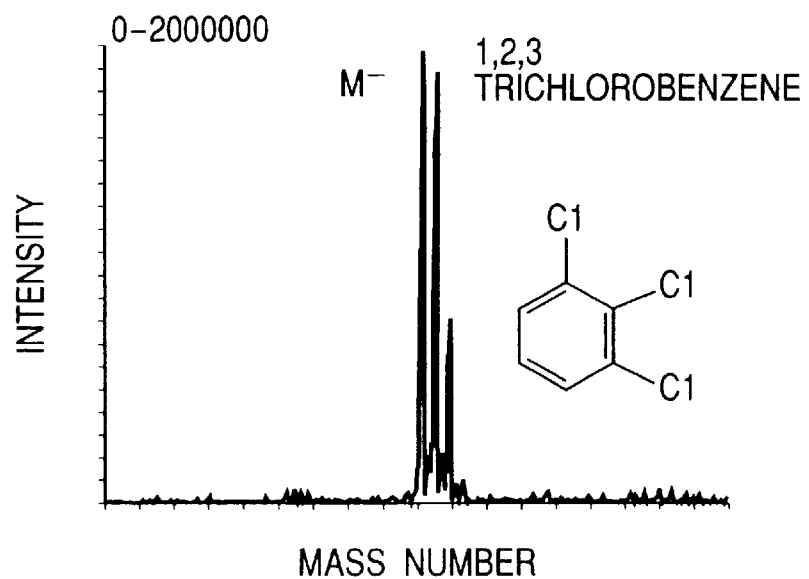
FIG. 25 is a diagram showing a typical mass spectrum of a chlorobenzene.
Figure 26:
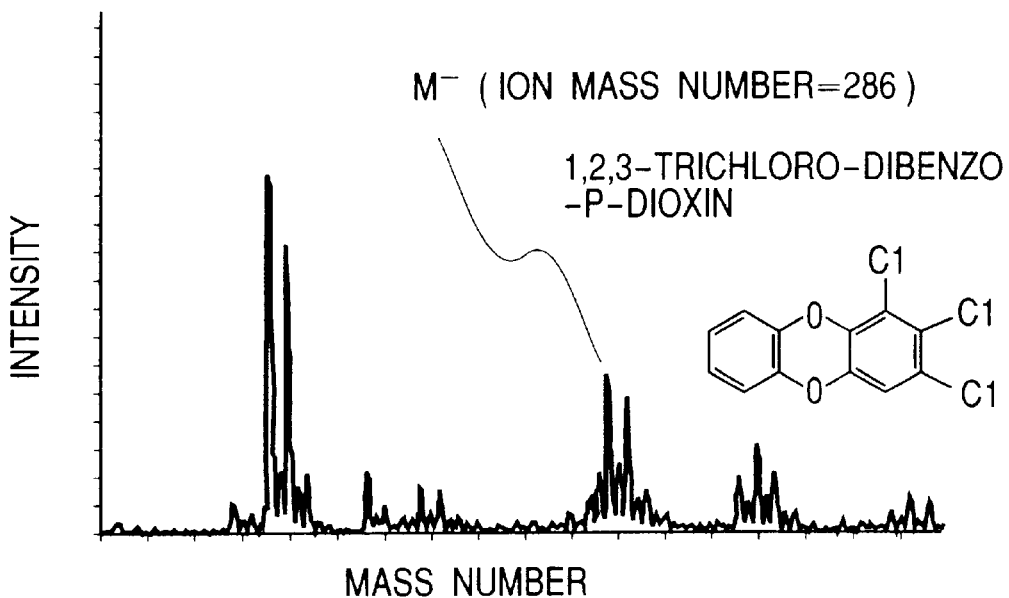
FIG. 26 is a diagram showing a typical mass spectrum of a dioxin.

The detected ion current is sent to the data processor 47 via the amplifier 50, and a mass spectrum is thereby obtained. An example of the mass spectrum obtained by the atmospheric pressure chemical ionization method of the present application is shown in FIG. 24 ($NO_2^-$, $NO_3^-$, etc.), FIG. 25 (case of 1,2,3-trichlorobenzene), and FIG. 26 (case of 1,2,3-trichlorodibenzo-para-dioxin). These spectra show ion currents (Y axis) corresponding to the mass numbers (X axis) of ions of components to be monitored. In the case of 1,2,3-trichlorobenzene, and 1,2,3-trichlorodibenzo-para-dioxin, plural isotope peaks are observed in the molecular ion part. This is due to the stable isotopes of the chlorine atom ($^{35}C$ and $^{37}C$, intensity ratio being 76:24). The measurement of the mass spectrum is usually completed in a short time of about 1 second to several tens of seconds. Mass spectrum measurements may also be repeated, and an average of the spectra taken to improve the S/N ratio.

Figure 28:
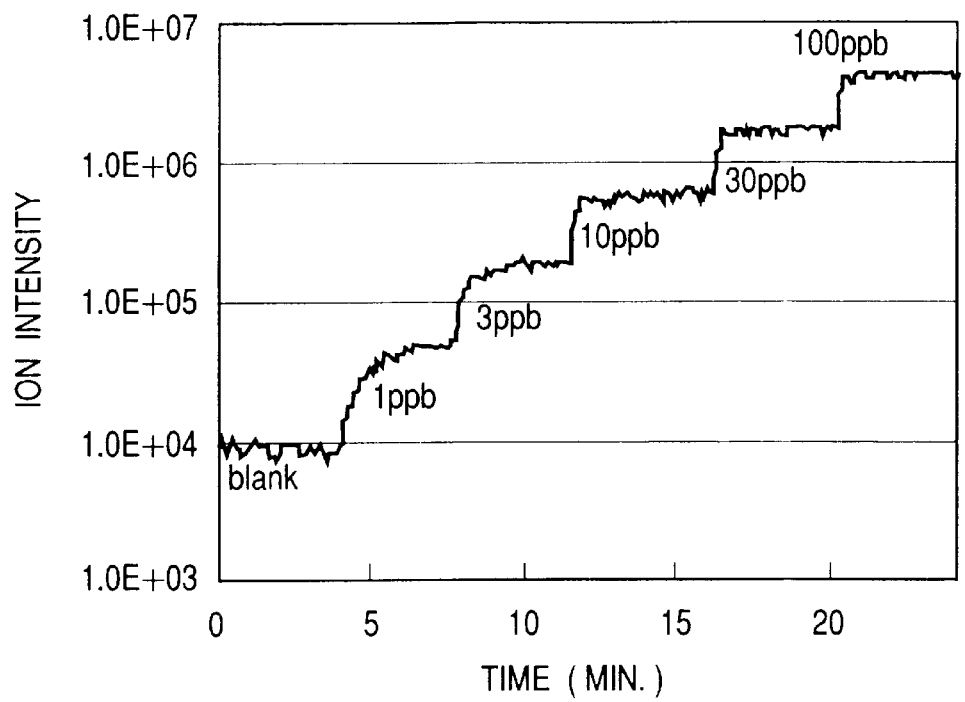
FIG. 28 is a diagram showing an example of measurement of a sensitivity curve.
Figure 29:
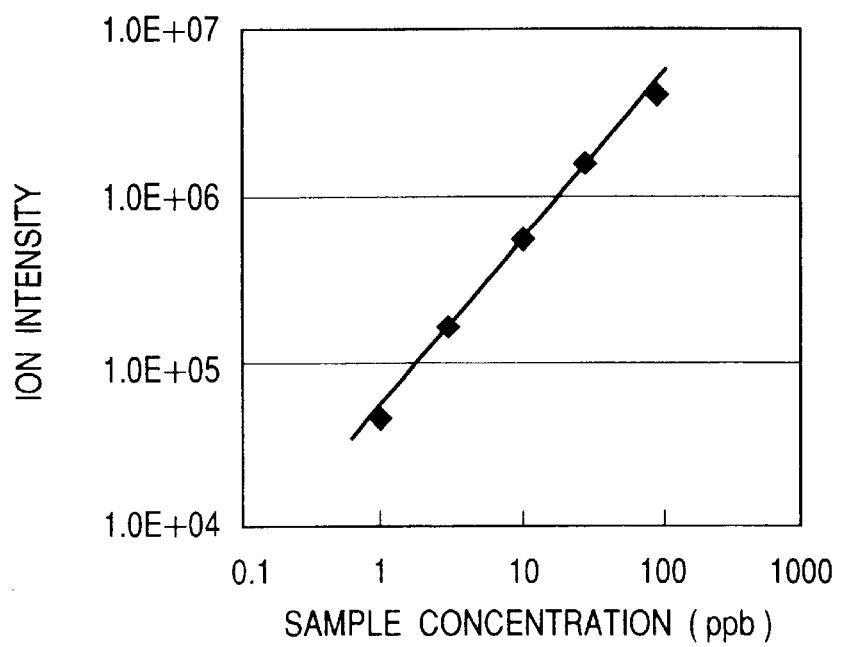
FIG. 29 is a diagram showing an example of measurement of a calibration line.

From the ion current for the mass number due to the substance to be measured, and a relation (calibration curve) between the amount and ion current of a standard substance prepared beforehand, the amount of a target substance can be calculated. For example, in the case of 2,3-dichlorophenol (molecular weight 162, observed ion mass number 161), a variation of ion intensity relative to concentration in the sample gas is measured as shown in FIG. 28, and a calibration curve shown in FIG. 29 is drawn. Based on this, concentration data in the sample gas at that time are estimated from the observed ion intensity. The obtained data are processed further, the concentration of the component is stored together with other parameters, and is output to a CRT or printer as necessary.

Chlorobenzenes which are precursors of dioxins capture one electron to produce a molecular ion $M^-$. Herein, a neutral molecule is represented by M, and a molecule which has captured an electron to become a negative ion is represented by $M^-$. Chlorophenols lose one proton of a phenoxy group (—OH group) to give the pseudomolecular ion (M—H). Dioxins give (M—Cl) and $(M—Cl+O)^-$ apart from the molecular ion M⁻, and they also undergo fragmentation to give a 1,2 orthoquinone type fragment ion. If these characteristic peaks are selectively detected, a high selectivity, high sensitivity measurement can be made.

The molecular weights and monitored ions of chlorobenzenes, chlorophenols and dioxins are shown in FIGS. 31A to 31C. As the natural isotopes of chlorine, 35 and 37, exist in the ratio of 3:1, the number of chlorine atoms contained in an ion can be estimated by observing this isotope pattern. Moreover, if plural isotope peaks are monitored and integrated, high precision monitoring is possible. For example, trichlorobenzene gives an isotope pattern of 27:27:9:1 to masses 180, 182, 184 and 186. If these ions are integrated, a high S/N ratio will be obtained as compared with the case when they are separate. In an actual measurement, all the ions in these tables may be monitored and the dioxin concentration estimated from their total amount, or only some of these ions may be monitored. For example, if only the ions present in largest amounts are monitored, simple, high sensitivity monitoring can be performed. Alternatively, if ions with 2 to 4 chlorine substitutions which contribute largely to the formation of dioxin are selectively monitored, simple, high precision monitoring can be performed.

In order to estimate the dioxin concentration from the concentration of chlorobenzenes and chlorophenols, a correlation between the two is used which is calculated beforehand. As the correlation differs somewhat depending on the type and model of incinerator, it is desirable to determine this correlation for every incinerator where a monitor is installed.

As shown in FIGS. 1 and 2, flue gas which has passed through the ion source 30 is passed through the waste gas pipe 5 by a waste gas pump 95 (diaphragm pump), and is returned downstream of the gas sampling probe 3 from the waste gas probe 2. This is so as not to discharge noxious flue gas indoors during measurement. The gas discharged by the vacuum pump 12 of the mass spectrometer is also collected by a vacuum pump waste gas pipe 96 (FIG. 2), and returned to the flue 1 together with flue gas which has passed through the ion source 30. The sampling part 88 and ion source 30 are made airtight to prevent leakage to the exterior, prevent entry of the atmosphere, and prevent disturbances.

The flue gas contains water, hydrogen chloride, sulfur oxides, high boiling components and tar, etc. in large amounts, and if condensation, adsorption or corrosion due to these substances has an adverse effect on measurements, it is effective to remove them by an impinger inserted into the pipe system.

Figure 17:
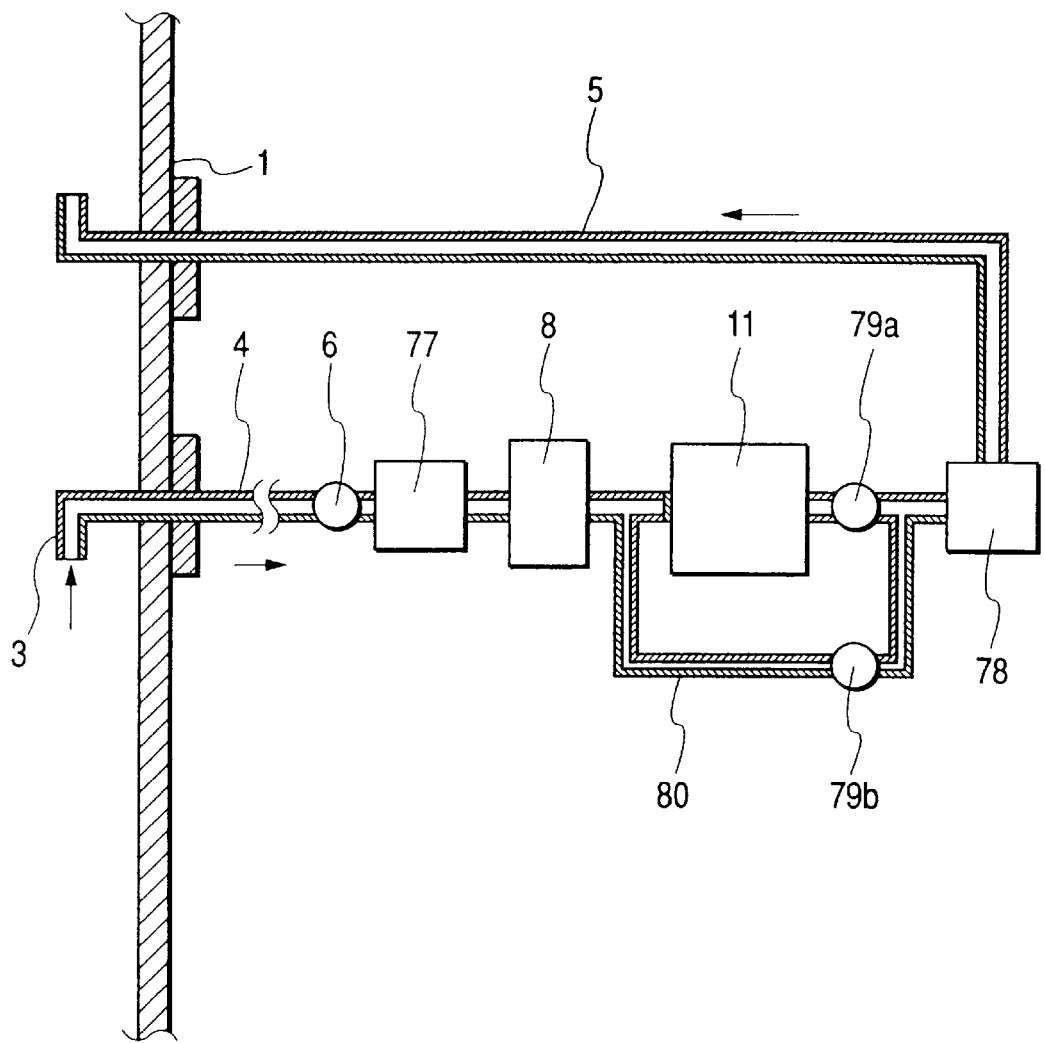
FIG. 17 is a diagram showing another arrangement of the monitor.
Figure 22:
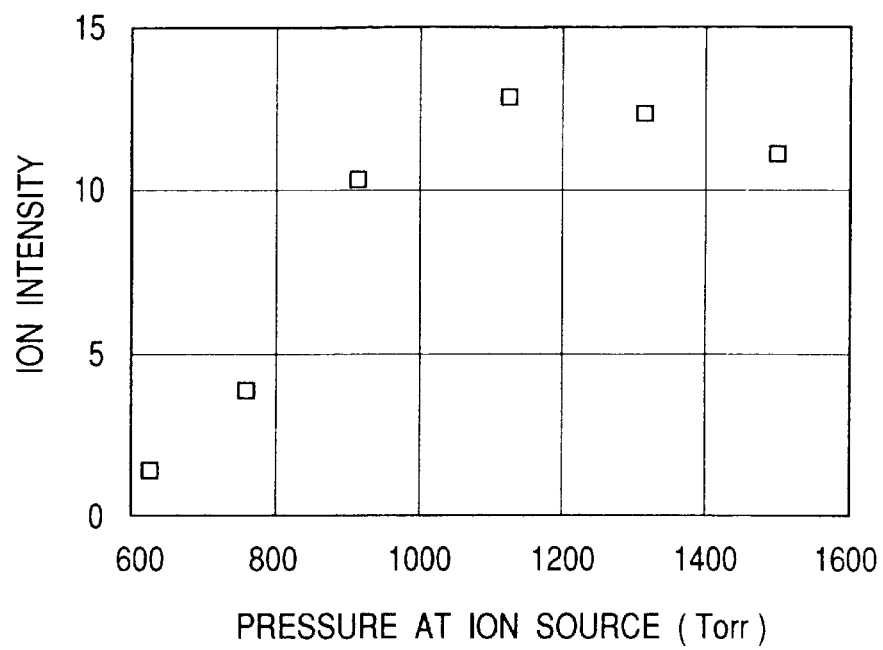
FIG. 22 is a diagram showing a relation between pressure and ion intensity in the atmospheric pressure ion source.
Figure 23:
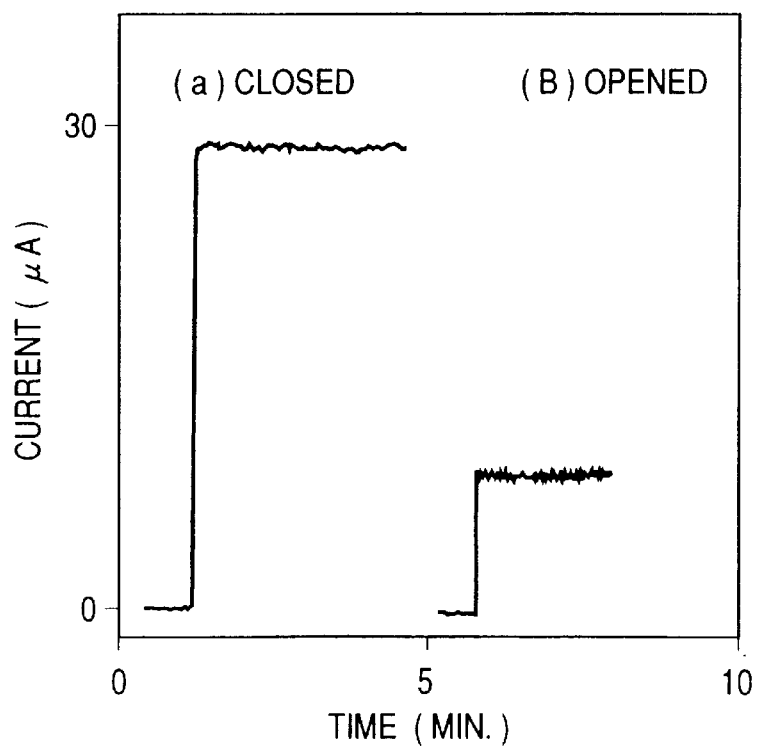
FIG. 23 is a diagram showing a relation between pressure and ion current in the atmospheric pressure ion source.

In the description given so far, when a sample gas was introduced into the monitor 11, the gas blow pump 8 was provided upstream. As shown in FIG. 17, the flowrate of sample gas introduced into the ion source is determined to be from several liters/minute to several tens of liters/minute by the blowing capacity of the gas blow pump 8, the needle valves 79a, 79b and the resistance of the branch pipe 80, and the pressure in the ion source can be increased by controlling the needle valves 79a, b. Normally, in an atmospheric pressure ion source which uses corona discharge, excess gas which does not flow in from the holes which take ions into the vacuum is expelled outside the ion source, so the corona discharge area is effectively at atmospheric pressure (approximately 760 Torr). Actually, the ionization efficiency increases to the extent that the molecular density in the corona discharge area is higher, and the optimum value of the pressure of the corona discharge area is higher than the atmospheric pressure of 760 Torr. However, if the pressure in the vicinity of the holes which take ions into the vacuum is too high, too many molecules will flow into the mass analysis part high vacuum through the holes, and it is difficult to maintain the high vacuum in the mass analysis part. FIG. 22 shows a relation between ion source pressure and ion intensity. It is seen that in the maximum of ion intensity occurs at a higher pressure than 760 Torr. FIG. 23 shows a sensitivity comparison between the case when the measurement is performed when the pressure of the corona discharge area is increased (approximately 1.2 atmospheres), and the case when the measurement is performed under effectively atmospheric pressure (approximately 1 atmosphere). The sensitivity is approximately three times higher in the former case than in the latter, showing that it is effective to increase the pressure in the ion source 30. To control the pressure inside the ion source, a pressure adjusting part may also be provided before the needle valve 79a, and the pressure of the corona discharge area of the ion source 30 controlled by this pressure adjusting part 97 while the pump 8 is operating.

Figure 16:
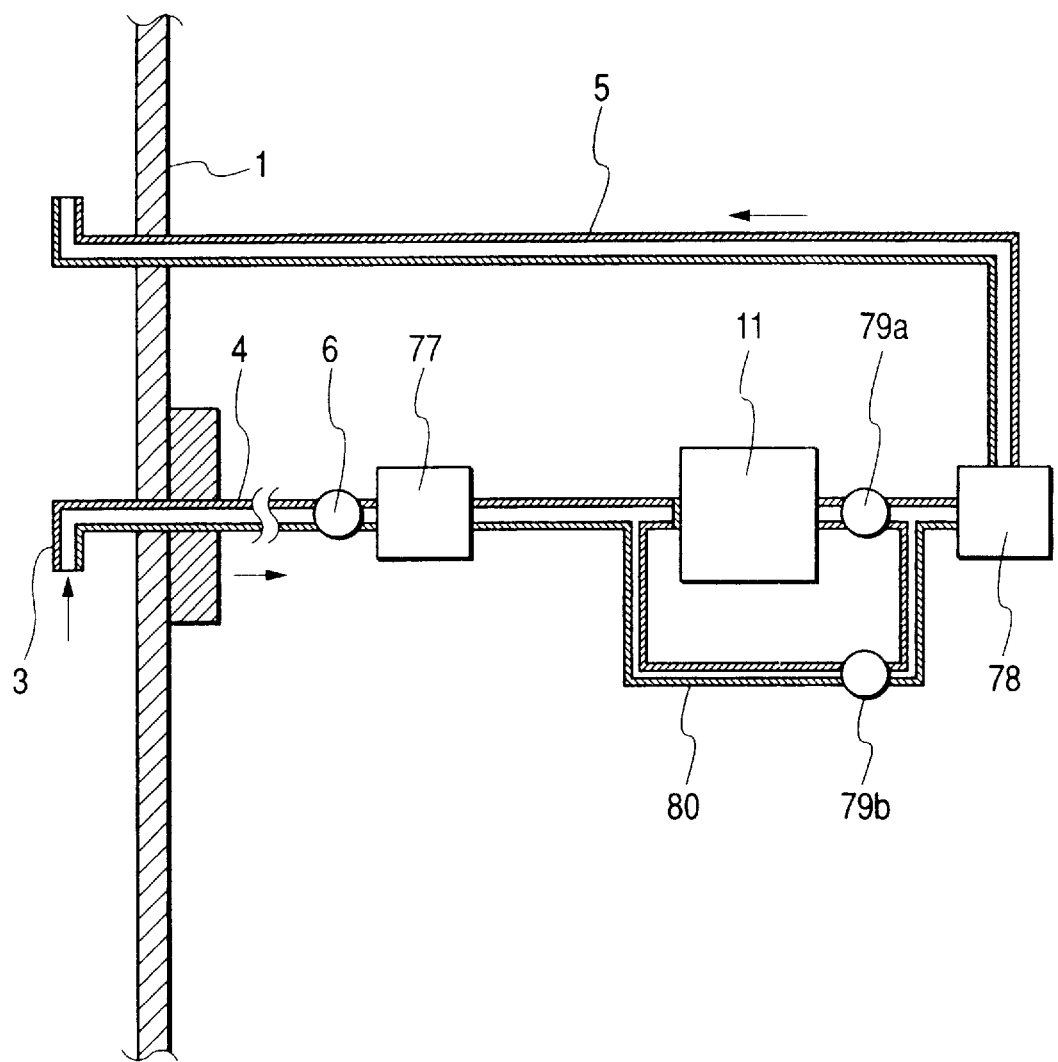
FIG. 16 is a diagram showing a typical arrangement of the monitor.

Alternatively, only a discharge pump 78 may be provided after the monitor 11 as shown in FIG. 16 to control the flowrate of sample gas entering the ion source 30 of the monitor 11 from several liters/minute to several tens of liters/minute. In this case, the flowrate is determined by the discharge rate of the pump 78, the needle valves 79a, b and the resistance of the branch pipe 80. It also possible to dispense with the branch pipe 80.

Figure 33:
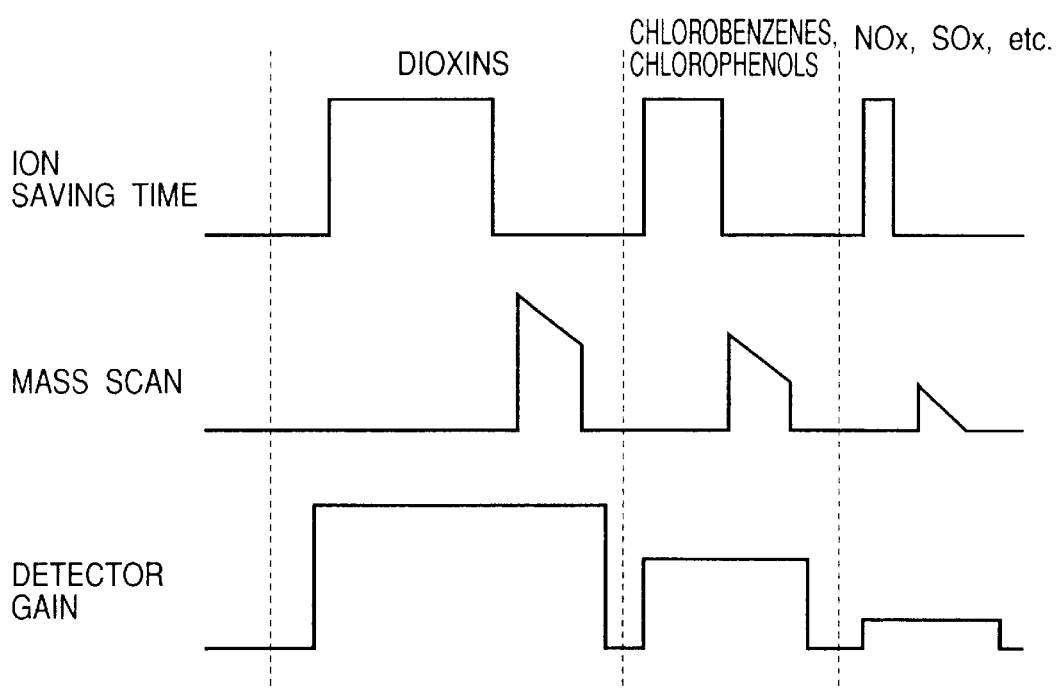
FIG. 33 is a diagram showing an example of a measurement sequence for dioxins.

FIG. 33 shows a flowchart for the measurement of dioxins. The gain of the detecting system is set to the highest sensitivity. Moreover, the ion introduction time is made as long as possible (from about several 100 msecs to several 10 secs). The ions derived from dioxins shown in FIG. 31C are monitored one after another. It is not necessary to monitor all the ions shown in FIG. 31C, and the number monitored can be reduced. Ions from components having the same number of chlorine atoms (e.g., m/z 320 and 322) are added to realize even a small improvement of the S/N ratio. Further, the currents of all the ions originating from dioxins are integrated (sigmaIm) and taken as the total amount of dioxins. After one dioxin ion monitoring cycle is complete, monitoring of dioxins is repeated. The number of repeat measurements may be set by an external device. Integration is performed as required starting from one cycle to improve the S/N ratio. When measurement of dioxins is complete, measurement of clorobenzenes begins. The sensitivity of the detector is set to medium sensitivity, and the ion introduction time is also set. The ions derived from chlorobenzene in FIG. 31A are monitored one after another. The results are integrated for monitored ions having the same number of chlorine atoms. In this way, a component distribution for isomers of chlorobenzenes can be calculated. All the ion amounts are also integrated (sigmaIm10) to calculate the total amount of chlorobenzenes. After one measurement cycle is complete, monitoring of chlorobenzenes is performed again and the ion amount is integrated. The number of repeat measurements may be one or more depending on the concentration. One cycle is completed in about 1 second. When measurement of chlorobenzenes is complete, monitoring of chlorophenols begins. For chlorophenols, the ions shown in FIG. 31B are monitored. Monitoring is repeated as in the case of chlorobenzenes, and the distribution of components and total amount of chlorobenzenes are calculated. After measurement of chlorobenzenes is complete, $NO_x$, $SO_x$, hydrogen chloride and oxygen, etc., are monitored. After measurements are complete, a comparison with previously measured values and mass spectra is made to determine whether an abnormal state exists. If an abnormal state exists, an alarm is output. This monitoring is performed in an endless loop, and monitoring conditions are changed by external devices as necessary.

Herein, measurements and embodiments were described concerning mainly the dioxin and related compounds in flue gas discharged from a garbage incineration plant. Measurements of dioxins and related compounds in flue gas from a metal refining process and the atmosphere can be made with the same equipment and methods. This monitoring device makes it possible to directly know how much dioxins are contained in flue gas, such as from an incinerator, and how much fluctuation there is. It permits real time dioxin monitoring and concentration measurement of dioxins in many locations in an incinerator. After combustion starts in the incinerator, the flue gas passes through a large number of different areas at different temperatures until it is discharged into the atmosphere from a flue, and many chemical reaction processes occur in the flue gas before it is discharged. Using this monitoring device, it is possible to follow dioxin formation and decomposition in each of these complicated processes. It is of course also possible to acquire information for changing and optimizing process conditions aimed at cutting down dioxins.

In the above-mentioned example, the ions produced by the negative corona discharge were introduced into the mass spectrometer after deflection, although they may of course be introduced into the mass analysis part without deflection.

Furthermore, although the case was described where an ion trap mass spectrometer was used as the mass spectrometer, other mass spectrometers, such as a quadruple mass spectrometer and a compact magnetic field type mass spectrometer, may also be used.

Embodiment 2

Figure 30:
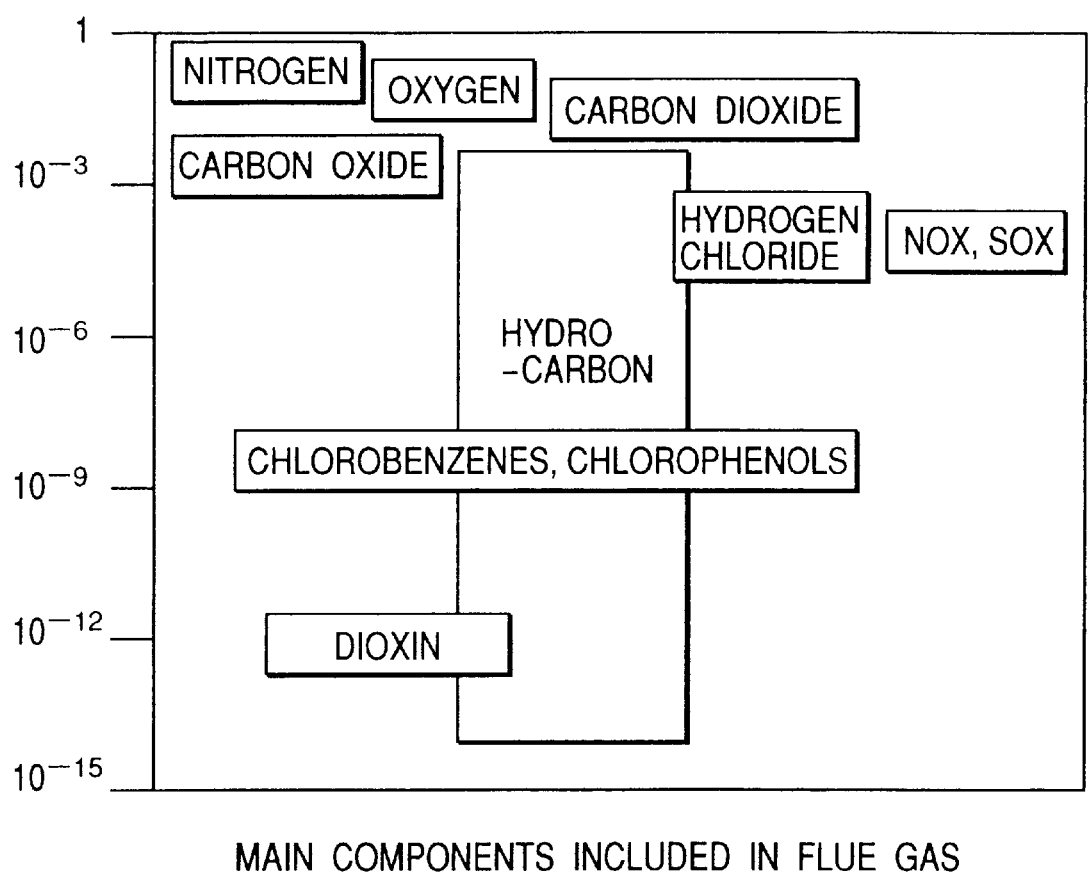
FIG. 30 is a diagram showing the main components of flue gas.

FIG. 30 shows the general abundance ratio of the main components contained in flue gas from a garbage incineration plant. The vertical axis shows abundance ratio. 1 represents 100%. $10^{-6}$ corresponds to ppm, $10^{-9}$ corresponds to ppb, and $10^{-12}$ corresponds to ppt. After oxygen, carbon dioxide and water which are present at % levels, carbon monoxide and hydrocarbons are present at a level of 1000 ppm. There are a large number of components in hydrocarbons and their concentrations are distributed over a wide range from 10 ppm to the 1 ppt level. Hydrogen chloride (250 ppm to 1300 ppm), $NO_x$, (100 to 200 ppm) and $SO_x$ (~100 ppm), etc., are present at a level of several 100 ppm. On the other hand, the concentration of chlorobenzenes and chlorophenols which are said to be precursors of dioxin is of the order of 1 ppb (1000 ng/Nm$^3$). The concentration of dioxins is below 10 ppt (10 ng/Nm$^3$). Thus, to directly measure target components such as dioxin precursors and dioxins in flue gas, high selectivity is essential to detect only minute amounts of the target components together with many interfering substances which are present in large concentrations. For this reason, it is very effective to use negative corona discharge and to use a mass spectrometer for detection of the ions produced. There are some cases when substances are present which are ionized by negative corona discharge in the same way and generate ions of the same ion mass number as the target components, and in these cases, detection of the target components alone is very difficult with a mass spectrometer using negative corona discharge.

Figure 27:
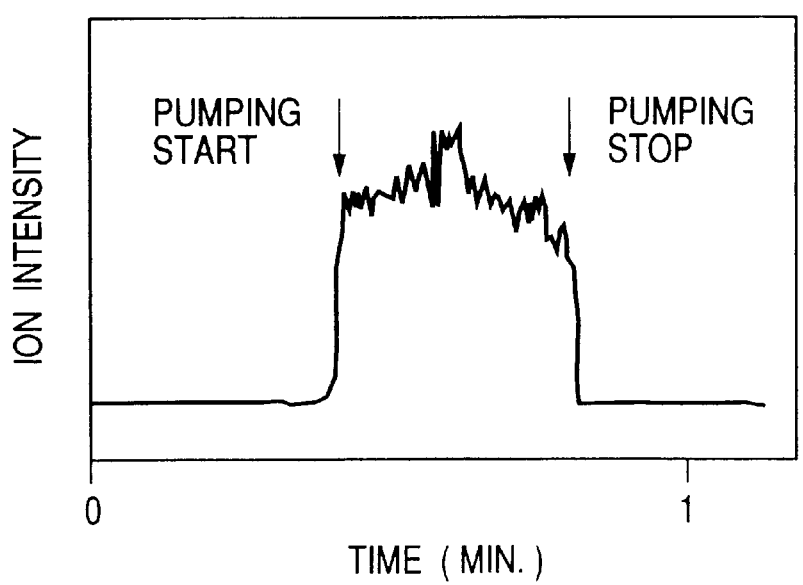
FIG. 27 is a diagram showing an example of detection of chlorophenols.

However, if an ion trap mass spectrometer is used, higher selectivity can be obtained than in an ordinary mass spectrum by dissociating the generated ions (removing certain component elements or groups from the ions) to convert them to ions of different mass number. This is the MS/MS method wherein, in addition to the high frequency voltage applied to the ring electrode 46 and endcap electrodes 45a, b from the high frequency power supply 100, energy is given to the trapped molecular ions from an auxiliary alternating current voltage applied to the endcap electrodes 45a, b from an auxiliary alternating current power supply 98, thereby causing the molecular ions to collide with the buffer gas (e.g., He) in the electrodes so that they dissociate. In practice, an alternating current voltage (amplitude less than V, applied time of the order of several tens of ms, frequency of the order of 50 to 500 kHz) having an identical or slightly different characteristic frequency to that of the trapped ions is applied to the endcap electrodes 45a, b. In the case of an organochlorine compound, ions are observed by the MS/MS method from which one or two chlorine atoms have been eliminated. For example, in the case of 2,4 dichlorophenol, as shown in FIGS. 31A and 31B, the negative ion (M—H)$^-$ (M: molecule, H: hydrogen) is produced by negative corona discharge. If this negative ion is dissociated by the MS/MS method, a negative ion is produced from which one chlorine atom has been eliminated. Observing this negative ion means observing a process wherein a negative ion is formed from which one chlorine atom has been eliminated via (M—H)$^-$ from M in dichlorophenol, and very high selectivity can be obtained. Therefore, dichlorophenol can be detected even if an interfering substance which is ionized by a negative corona discharge and produces an ion of the same mass number, exists. In this case, a chromatogram (showing the variation of ion intensity with time) as shown in FIG. 27 is obtained, and if the amount of the negative ion from which one chlorine atom was eliminated is measured from the intensity of this peak, the amount of dichlorophenol in flue gas can be estimated. When there are plural molecular species to be measured, this measurement process may be repeated. In the case of dioxins, a COCl desorption process is observed in addition to dechlorination. Desorption of COCl is a process observed only in dioxins, and if this process is observed, it can be said to prove that TCDD or highly toxic dioxins are present. When there are plural molecular species which are to be measured, measurement by the MS/MS method may be repeated, but measurements may also be carried out simultaneously as follows. Taking chlorophenols as an example, the negative ions of di-, tri-, tetra- and pentachlorophenol produced by corona discharge are selectively trapped in the mass analyzing part. This is done by applying a white noise auxiliary alternating current which does not contain the characteristic frequency of the ion group to be trapped, to the endcap electrodes 45a and b, as stated previously. Next, an auxiliary alternating current comprising superimposed auxiliary alternating currents which are identical to or slightly different from the characteristic frequencies of the trapped ions, is applied to the endcap electrodes 45a, b to supply energy to the trapped molecular ions, and ions wherein a chlorine atom has been eliminated from the above-mentioned negative ions of chlorophenol, are thereby produced. The sum of the intensities of the ions corresponding to mono-, di-, tri- and tetrachlorophenol corresponds to the total amount of chlorophenols which is to be calculated.

In an actual incinerator, in the case of chlorophenols, di-, tri- and tetrachlorophenols account for at least 50% of the total amount of chlorophenols, therefore the amount of chlorophenols can be represented by the amount of di-, tri- and tetrachlorophenols instead of measuring all the chlorophenols. This reasoning can also be applied to chlorobenzenes and dioxins.

Embodiment 3

Figure 15:
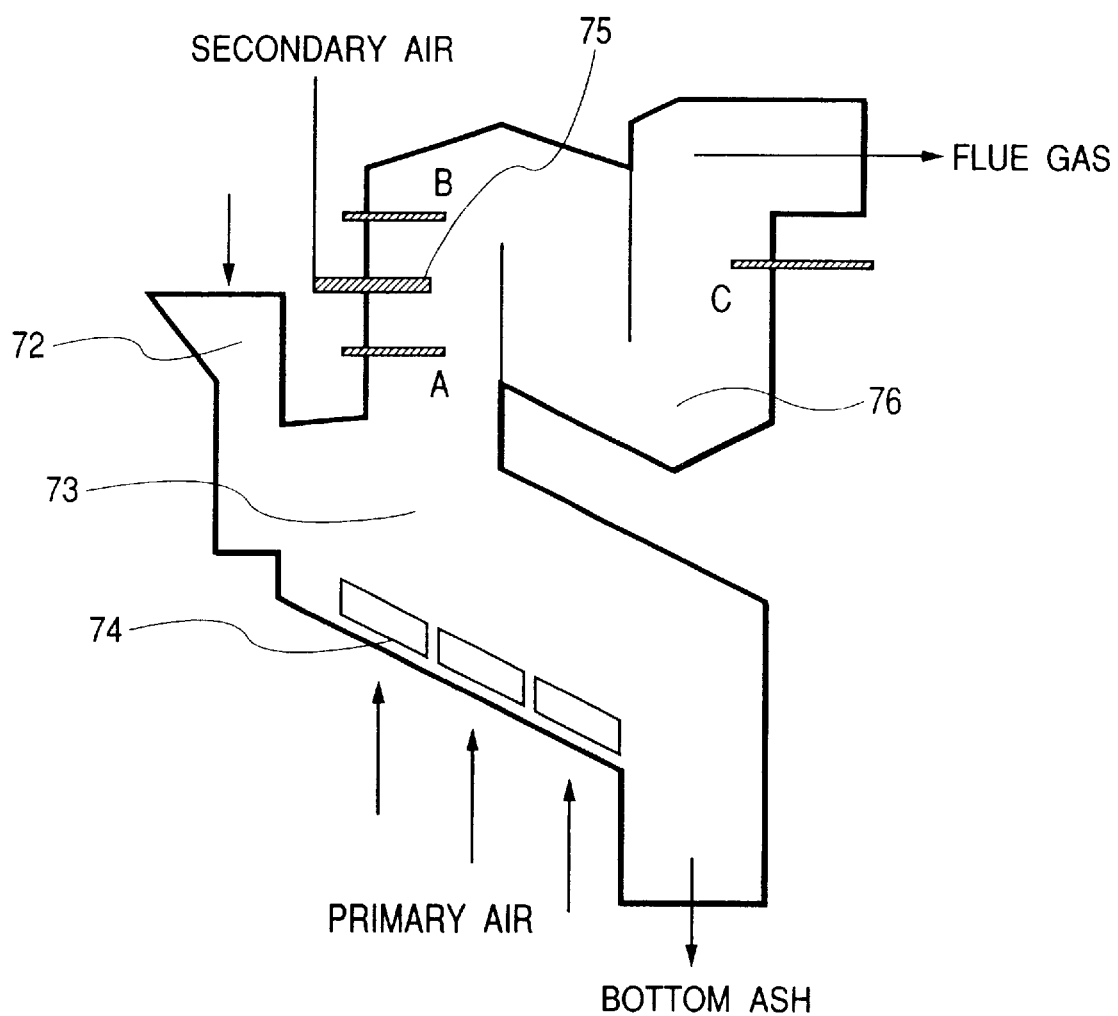
FIG. 15 is a diagram showing monitor observation points.
Figure 18:
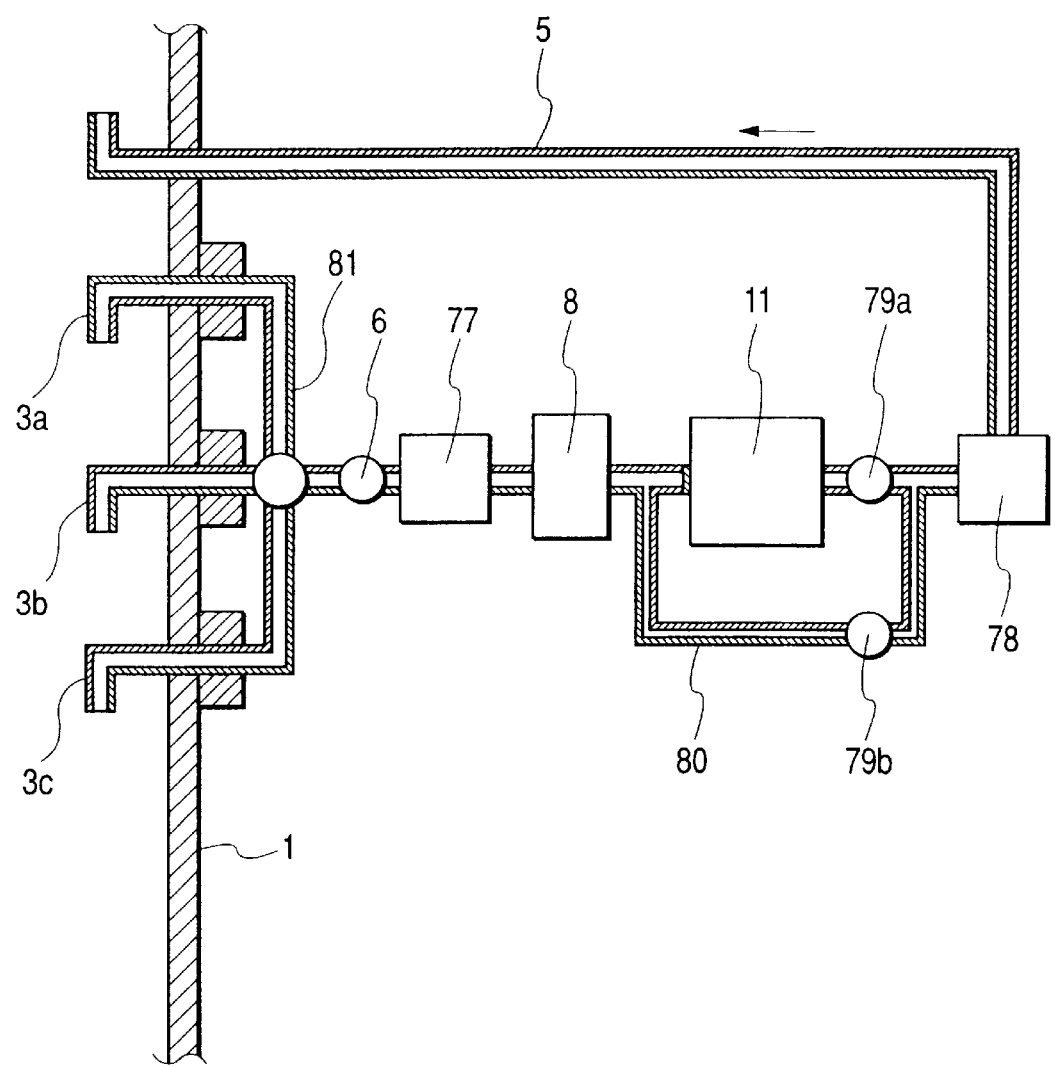
FIG. 18 and FIG. 19 are diagrams showing other arrangements of the monitor.
Figure 32:
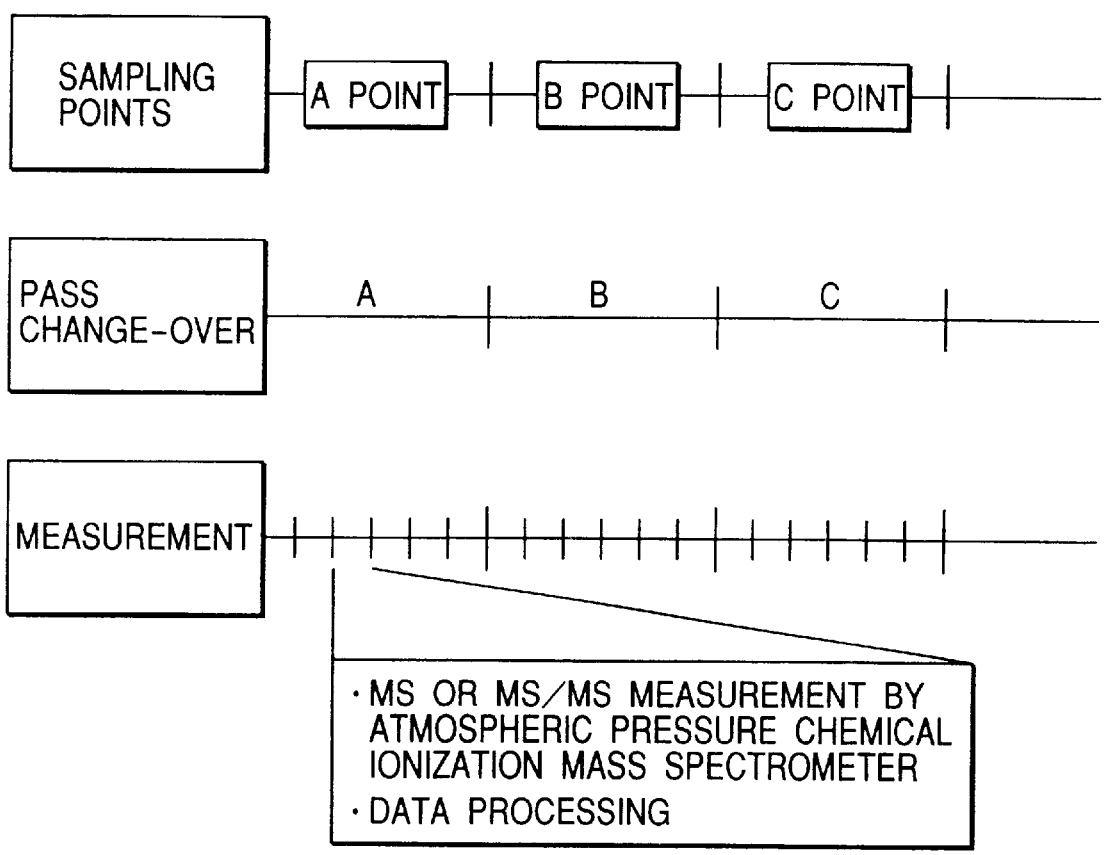
FIG. 32 is a diagram showing an example of the operation of a monitor.

Although measurements can be made continuously at one gas sampling point in a garbage incineration plant for a long period of time, combustion control conditions can be better grasped by increasing the number of measurement points. FIG. 15 is a schematic view of a garbage incineration plant. Garbage thrown into a hopper 72 is dried, thrown into a furnace 73 having a large number of grates 74, and burnt by primary air supplied from underneath. The combustion gases are mixed up in the furnace 73, and burn. Secondary air is blown into the combustion gases from a secondary air nozzle 75 to complete the combustion. Next, the hot combustion gases are led to a boiler 76 where heat recovery is performed. Due to the high temperature of the secondary combustion resulting from supply of secondary air, most organic compounds and organochlorine compounds are decomposed. However, although organochlorine compounds decrease, more $NO_x$, etc., is generated by the secondary combustion. If the gas sampling points A and B of the present application are provided in this area, the fluctuation in the concentration of $NO_x$, dioxins and organochlorine compounds due to secondary air injection and combustion temperature can effectively be monitored in real time. It is thus possible to operate the incinerator so that the occurrence of $NO_x$ and dioxins is inhibited. By monitoring a point B before the boiler 76 and to a point C after it, information can be gained regarding the generation and behavior of $NO_x$ and dioxins inside the boiler. Further, if monitoring is performed before and after the introduction of adsorbents such as active carbon and slaked lime, the amount of these additions can be geared to higher efficiency, the amounts added can be reduced, and cost reductions can be achieved. When measurements are performed at a large number of points by time sharing, the flowpath is changed over by a flowpath change-over valve 81 as shown in FIG. 18. In FIG. 18, the case of three measurement points is shown, but the number of measurement points can be increased further. The operating state of an actual monitor is shown in FIG. 32. If monitoring of plural points is changed over by the flowpath change-over valve 81 with time sharing, one monitoring device is sufficient. To sample at point A, the flowpath is changed over to point A. Monitoring is completed in about several seconds to several tens of seconds, but measurements are repeated to improve the S/N ratio and smooth the signal. The number of repeat measurements can be set freely as required. When monitoring of point A is completed in several seconds to several minutes, the flowpath change-over valve is changed over and monitoring moves on to point B. If there are a larger number of measurement points and the time for one measurement is about 30 seconds, even measurements at ten points can be performed in a cycle of 5 minutes. Also, flue gas should be made to flow continuously through the piping in the flowpath being measured, and through piping in other flowpaths not being measured, to avoid adsorption of components present in small amounts by the piping system, temperature variations, and pressure variations.

Embodiment 4

Figure 19:
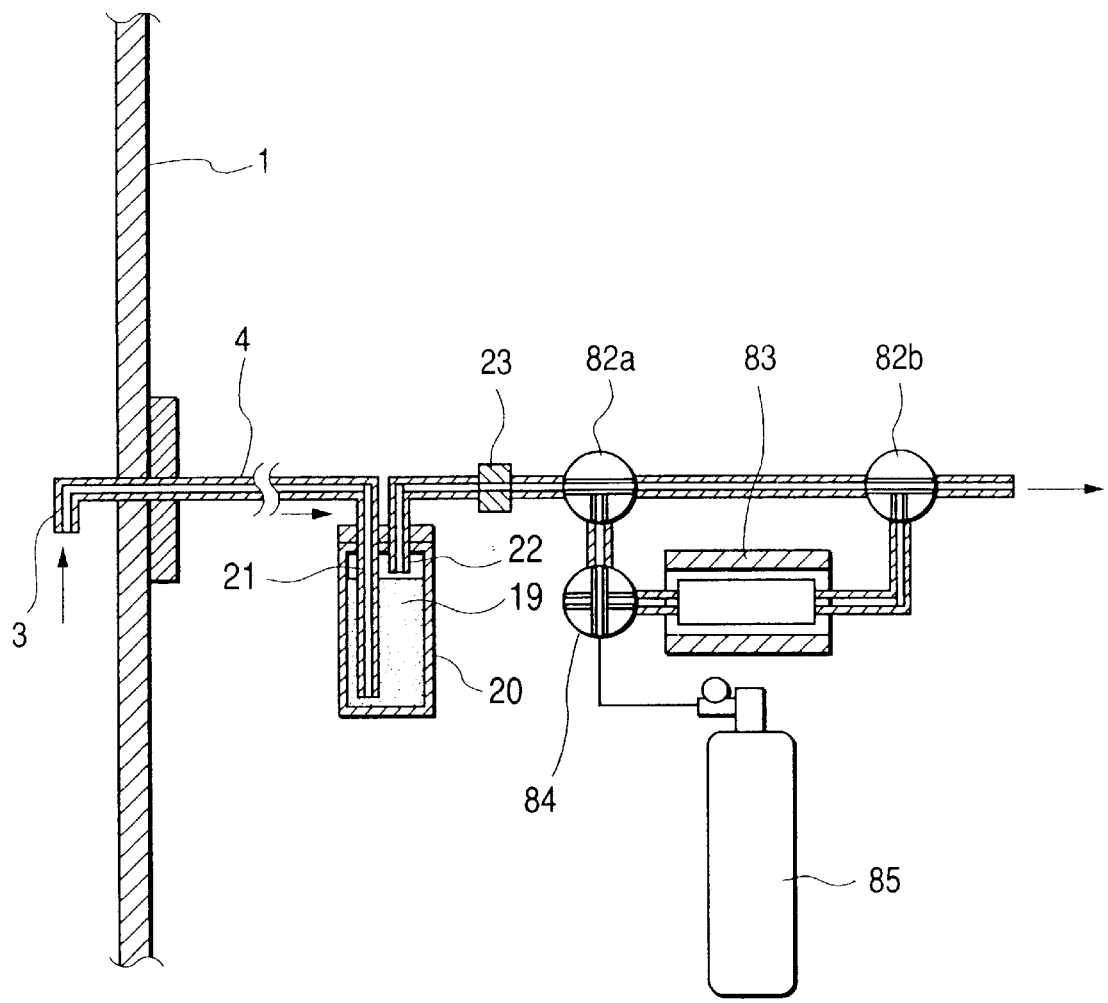

In the case of dioxin measurements in the atmosphere, etc., the dioxin concentration is still less as compared with the flue gas of a garbage incineration plant. It is therefore difficult to detect dioxin even if a sample gas is directly introduced to the ion source. In this case, a trap column 83 for trapping dioxin can be inserted in the gas sampling path, as shown in FIG. 19. Trap column 83 also represents a plurality of trap columns that can be inserted into the gas sampling path. After the dioxins have been adsorbed and concentrated, the flowpath is changed over to desorb the dioxins which are then detected. In this case, if high purity nitrogen gas or air in a cylinder 85 is used as a carrier gas for desorption, moisture, carbon dioxide and hydrocarbons, etc., in the gas can be eliminated. For monitoring substances present in high concentration such as $NO_x$, and $SO_x$, flue gas may be introduced to the ion source without modification, adsorption and concentration being performed only for components present in minute amounts like dioxins.

This will be described referring to FIG. 19. Sample gas is extracted by the gas sampling probe 3 inserted in the flue 1, and ash, etc., is removed by the dust filter 20 and the metal filter 23. Chlorobenzenes and chlorophenols, etc., which are present in high concentration in the sample gas, pass through a three-way cock 82a, piping and a three-way cock 82b, and are sent directly to the monitor part 11 where they are monitored. When dioxins are monitored, the three-way cocks 82a, b are changed over. The sample gas then passes through piping, a four-way cock 84, the trap column 83 and three-way cock 82b, and is led to the ion source 30. The dioxins are adsorbed and concentrated by the trap column 83. When a trap concentration time of about several minutes to several tens of minutes has elapsed, the four-way cock 84 is changed over, and nitrogen gas from the nitrogen cylinder 85 is passed through the trap column 83. At the same time as the four-way cock 84 is changed over, the trap column 83 is rapidly heated by energizing a column heater 99 surrounding the trap column. Dioxins adsorbed by the trap column 83 are then desorbed, and led to the ion source 30 where they are ionized and monitored. For high concentration components, the gas may be directly connected, whereas to monitor components present in medium concentration or in very low amounts, plural trap columns may be prepared and monitoring performed separately for each component. For example, different trap times may be used, e.g., 10 seconds for medium concentration components and 100 seconds for components present in very low amounts.

Embodiment 5

By using a calibration curve, the ion current measured by the monitoring apparatus is converted into a concentration of a dioxin or an organochlorine compound. For this purpose, the change-over valve 24 for introducing a standard sample is periodically changed over as required, or once a day, etc., to introduce a fixed amount of a standard substance together with a suitable gas from a chemical cylinder, not shown, or the standard sample generator 10, and automatic calibration of the monitor is performed. As the standard substance, a volatile organochlorine compound such as a chlorobenzene or a chlorophenol may be used, or $NO_x$, $SO_x$, etc., may be used. The signal obtained by introducing the sample substance is compared with a value which was previously input or a previously measured value, and if there is a large deviation, an alarm is output and calibration is performed.

Embodiment 6

During on-line measurement or whenever necessary, e.g., once a day, a self-test is performed as to whether there are any abnormalities in measured signals, the background, temperature of the flue gas, pressure or flowrate, etc., and required operations, such as automatic cleaning, automatic calibration, issue of device fault alarms or device shutdown, are performed.

Embodiment 7

Figure 34:
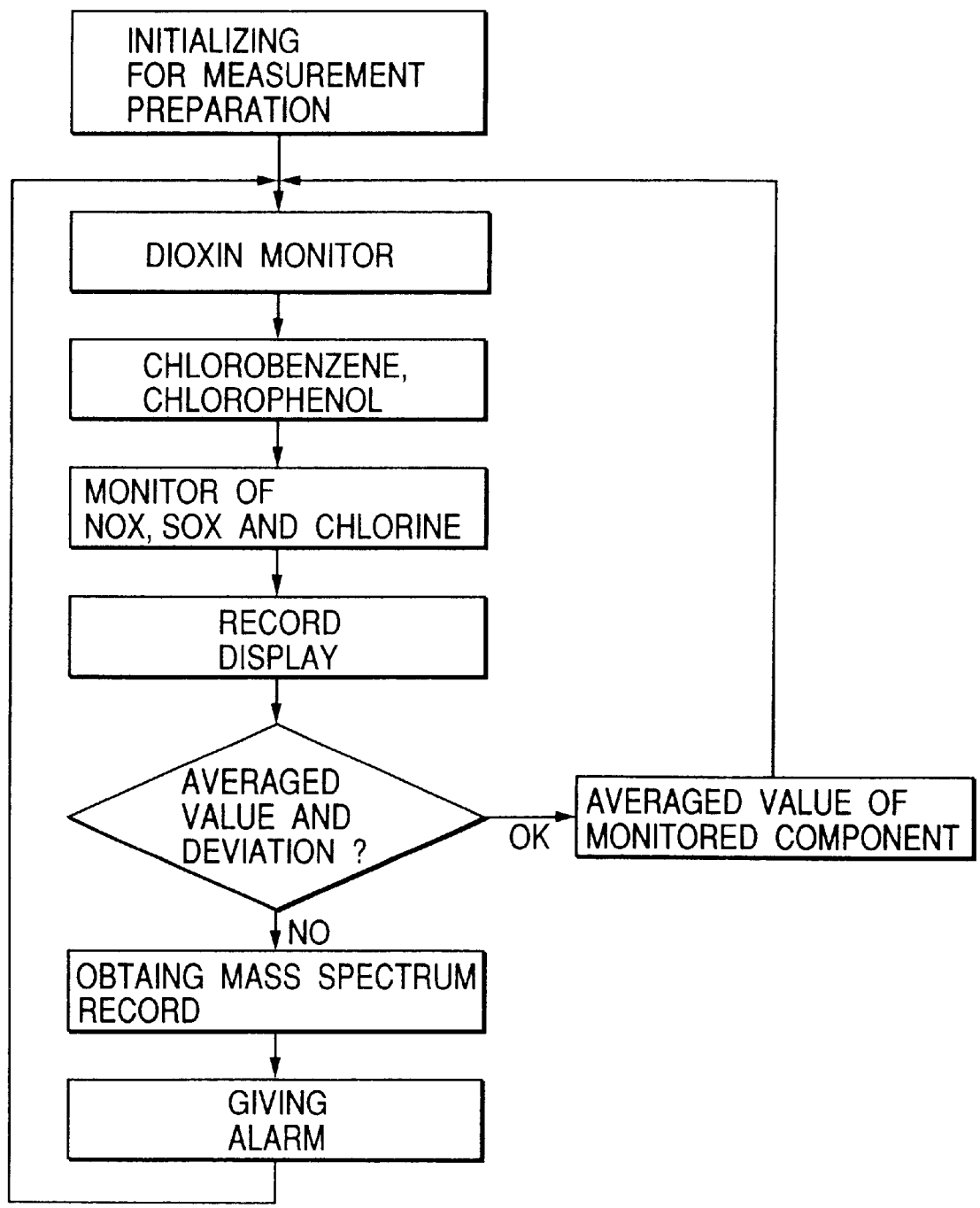
FIG. 34 is a flowchart of a typical measurement sequence.

To detect short-term abnormalities, another process is required. This constantly determines whether or not there are faults, as shown in FIG. 34. The determination may be performed by manually inputting an average value for the incinerator from an I/O device beforehand, or by repeating measurements to automatically calculate an average value. In FIG. 34, a method of automatically calculating an average value is shown by a flowchart. After sequentially determining dioxins, chlorobenzenes and chlorophenols, the value of each component is compared with an average value. If the deviation is greater than a predetermined value, an alarm is output by an I/O device or alarm instrument, and measurement is repeated. If the alarm is repeated, a higher level alarm is issued, and self-diagnosis, calibration and monitoring apparatus shutdown are performed.

The components causing the abnormal value are likely to be contained in the flue gas, therefore, the trace component monitoring apparatus shifts to a different determining mode from ordinary monitoring. When there is a fault condition, the mass spectrometer performs a mass scan to acquire mass spectra. These are then filed and recorded together with other parameters, and displayed on the I/O device. The blow volume of primary air or secondary air supplied to the furnace is adjusted by the combustion controller 15 while monitoring the situation, and emission of dioxins, chlorobenzenes and chlorophenols is suppressed. This determination also aids in identifying the cause of the abnormal condition.

Mass spectra are obtained not only in abnormal conditions. If a mass spectrum scan is included in the monitoring cycle for dioxins, and mass spectra are constantly acquired as monitoring is performed, the state of the furnace can be known at any time. For example, if a large amount of garbage containing water is incinerated, large peaks due to water ions appear in the mass spectrum, and if a large amount of vinyl chloride is incinerated, large peaks due to chlorine ions appear in the mass spectrum. If a mass spectrum is periodically interspersed in the monitoring of components present in very small amounts and this mass spectrum is observed, an abnormal state can be detected. The measured mass spectrum is compared with a previously measured mass spectrum (comparison mass spectrum), and if a new mass peak appears or a large mass peak disappears, it is determined that an abnormal state exists. Specifically, the intensities of mass peaks having the same mass/charge ratio (m/z) on the spectra to be compared are subtracted from one another. If there is no peak on a mass spectrum, the intensity is taken to be 0. If a large peak appears on the difference spectrum, it signifies a component that has suddenly appeared in the flue gas, so this is regarded as abnormal and an alarm is output.

The measured data are processed by data processing, and filed and stored together with set values or experimental values of combustion conditions. If there are parts showing values exceeding the reference values, they are color-coded, e.g., with red or pink, and an alarm is immediately output to the operator. If necessary, the data are output to a printer or CRT, and also sent to an incineration surveillance and control system.

Embodiment 8

During measurements, flue gas is allowed to flow continuously through the atmospheric pressure ion source and piping to maintain an equilibrium in the exchange of gas and substances adsorbed on the wall surface, and eliminate adsorption of components present in very small amounts on the wall surface. When the flow of flue gas is stopped during shutdown of the incinerator, maintenance inspections or filter replacement in the sampling system, high purity nitrogen gas is automatically circulated to prevent soiling of the atmospheric pressure ion source or piping. Also, depending on the state of soiling of the ion source or piping, a purge gas such as a high purity gas is circulated, for example once a week, to perform automatic cleaning of the ion source and pipes. When the emission of the standard sample from the standard sample generator 10 in the monitoring apparatus shown in FIG. 1 is stopped, nitrogen gas from a nitrogen cylinder, not shown, is passed through the valves, piping and the ion source 30 without modification to perform cleaning. The device is periodically cleaned by allowing nitrogen gas to flow periodically when the device is started or stopped, or during measurement. The nitrogen gas may be introduced into the gas sampling unit 88 separately from the standard sample introduction system. If flue gas is introduced and measurements are begun after passing pure nitrogen through the system, the flue gas is allowed to flow for at least 30 minutes to prevent adhesion to the pipe walls.

Embodiment 9

FIG. 30 shows abundance ratios for the main components included in flue gas. The vertical axis shows the abundance ratio. 1 represents 100%. $10^{-6}$ represents ppm, $10^{-9}$ represents ppb and $10^{-12}$ represents ppt. After nitrogen, oxygen, carbon dioxide and water which are present at % levels, carbon monoxide and hydrocarbons are present at a level of 1000 ppm. Hydrocarbons contain many components, and their concentrations are distributed over a wide range from 10 ppm to 1 ppt. Hydrogen chloride (250 to 1300 ppm), $NO_x$, (100 to 200 ppm) and $SO_x$ (~100 ppm) are present to the extent of several hundred ppm. On the other hand, the concentration of chlorobenzenes and chlorophenols which are said to be dioxin precursors, is said to be of the order of 1 ppb (1000 $ng/Nm^3$). The concentration of dioxins is below 10 ppt (10 $ng/Nm^3$). Inorganic compounds containing highly electronegative elements such as oxygen, sulfur and halogens (F, Cl, Br and I) (nitrogen oxides ($NO_x$), sulfur oxides ($SO_x$), chlorine ($Cl_2$), hydrogen chloride (HCl)) are also present in flue gas to the extent of several hundred ppm. These substances are also noxious substances of which the discharge into the atmosphere is regulated. Moreover, by using negative ion mode atmospheric pressure chemical ionization, in addition to these substances, oxygen and water can be ionized and measured in the same way as dioxins and organochlorine compounds such as chlorophenols and chlorobenzenes.

$NO_x$, and $SO_x$ are present in high concentrations 108 to 109 times greater than the concentration of dioxins. Therefore, even if the ionizing efficiency is somewhat inferior, the amount of such ions detected is far greater than that of dioxins, and consequently, it is not the best policy to measure dioxins, chlorophenol and chlorobenzene at the same time as $NO_x$, and $SO_x$. In this case, the mass spectrum of $NO_x$, and $SO_x$ is obtained at low sensitivity in one mass analysis (one mass scan), the mode is changed over to medium sensitivity and measurement of chlorobenzenes and chlorophenols is performed, and finally, the mode is changed over to high sensitivity and a mass analysis of dioxins is performed.

There are several methods of changing over the sensitivity. FIG. 33 shows the case where the mass spectrometer is an ion trap mass spectrometer. By adjusting the time during which ions are introduced to and accumulated in the ion trap mass analyzer from an external device, a large dynamic range can be covered. When the ion current is small, the ion accumulating time is lengthened. Conversely, when there is a large ion current, the ion accumulating time is shortened. After introducing and accumulating ions, a mass scan is performed and a mass spectrum is obtained. The detector is also synchronized, and is switched between low, medium and high gain to perform measurements. If measurements are alternately repeated while switching through the three sensitivities, dioxins, chlorobenzenes, chlorophenols, $NO_x$, and $SO_x$, etc. can effectively be measured in real time. Dioxins are present only in extremely low amounts as compared with chlorobenzenes and chlorophenols, or $NO_x$ and $SO_x$. For this reason, these three groups of substances are not monitored equally, the number of measurements in one cycle is increased in the case of dioxins which are present in only very small amounts, and the data are smoothed. The frequency of monitoring between the three groups may also be varied.

Embodiment 10

In the above example, the case was mainly described where negative ion atmospheric pressure chemical ionization is used. Various components are present in flue gas, but for hydrocarbon compounds, such as olefinic hydrocarbons or aromatic compounds typified by benzene, etc., or compounds with low numbers of chlorine atoms, measurements can also be made by positive ion mode atmospheric pressure chemical ionization. For example, with benzene and monochlorobenzene, the ion species M+ is generated by positive ion atmospheric pressure chemical ionization. Other ion species observed in positive ion mode are $(M+H)^+$, etc.

The ions derived from hydrocarbons obtained by the positive ion mode represent the combustion state of the furnace, and may also be used as an indicator of incomplete combustion like carbon monoxide. Specifically, when ions derived from hydrocarbons with high molecular weight are observed in large quantities, it can be presumed that combustion is inadequate. Further, in actual sample gas monitoring, it is also effective to increase the amount of information during gas sampling by making measurements alternately in the positive and negative ionization modes.

Embodiment 11

In the above-mentioned example, the description focused mainly on removing solids, such as ash, from the dust filter part, but filters may also be provided for removing gaseous components present in large amounts such as hydrogen chloride. In an ordinary incinerator, the composition of gas produced by burning garbage may vary. In such a case, it is effective to provide a filter before the monitor part 11 for removing large amounts of gaseous components and suppressing large fluctuations of gas component composition. For example, in the case of hydrogen chloride, if a filter filled with calcium carbonate or slaked lime is provided, the level of hydrogen chloride falls to several 100 ppm even if it originally exceeded 1000 ppm, so interference with the ionization of target substances by a large amount of hydrogen chloride gas is mitigated, and monitoring is made easier.

Atmospheric pressure chemical ionization using a negative corona discharge is a high sensitivity, high selectivity ionization technique which can selectively ionize organochlorine compounds or compounds containing highly electronegative elements in the presence of large numbers of interfering substances. By combining this with ion trap mass spectrometry, an even more highly sensitive and selective monitoring method is obtained. Hence, this application permits direct monitoring of dioxins, dioxin precursors (chlorobenzenes and chlorophenols) and $NO_x$, $SO_x$ in flue gas by directly sampling gas from the flue.

What is claimed is:

1. A monitoring apparatus for chemical substances comprising:

a first piping for passing flue gas including a sample gas therethrough;

filter means for filtering solid impurities and ash in the flue gas including the sample gas, said filter means being provided on said first piping;

first and second changing-over means being provided separately from each other on said first piping;

a second piping being connected between said first changing-over means and said second changing-over means;

concentration means for concentrating dioxins included in said sample gas, which is provided on said second piping, and which comprises plural trapping columns each for trapping dioxins;

third changing-over means which is provided on said second piping between said first changing-over means and said concentration means;

a gas cylinder containing a carrier gas and connected to said third changing-over means;

an ion source, connected on said first piping, for ionizing said sample gas; and a mass spectrometer for mass analyzing ions produced in said ion source, wherein, when a monitoring for chemical substances present in high concentration in the sample gas is effected, the sample gas is directly introduced into said ion source, the sample gas passes through said filter means, said first changing-over means and said second changing-over means, in this sequence, and then the sample gas is introduced to said ion source, wherein a different concentrating time for concentrating dioxins is used for each of said plural trapping columns, and wherein, when a monitoring for dioxins desorbed from said trapping columns is effected, the sample gas passes through said filter means, said first and said third changing-over means and said trapping column, in this sequence, and then the sample gas is introduced to said ion source.

2. A monitoring apparatus for chemical substances according to claim 1, wherein said ion source includes an atmospheric pressure chemical ion source.

3. A monitoring apparatus for chemical substances according to claim 1, wherein said mass spectrometer is provided with an ion trap mass analyzing part.

* * * * *